(12) United States Patent
Holsinger et al.

(10) Patent No.: US 8,106,059 B2
(45) Date of Patent: Jan. 31, 2012

(54) SUBSTITUTED PYRAZINES THAT INHIBIT PROTEASE CATHEPSIN S AND HCV REPLICATION

(75) Inventors: Leslie Jean Holsinger, Los Altos, CA (US); Kyle Elrod, Belmont, CA (US); John O. Link, San Francisco, CA (US); Michael Graupe, Pacifica, CA (US); In Jong Kim, Lexington, MA (US)

(73) Assignee: ViroBay, Inc., Menlo Park, CA (US)

( * ) Notice: Subject to any disclaimer, the term of this patent is extended or adjusted under 35 U.S.C. 154(b) by 524 days.

(21) Appl. No.: 12/256,370

(22) Filed: Oct. 22, 2008

(65) Prior Publication Data

US 2009/0270415 A1    Oct. 29, 2009

Related U.S. Application Data

(60) Provisional application No. 60/982,278, filed on Oct. 24, 2007, provisional application No. 61/037,656, filed on Mar. 18, 2008.

(51) Int. Cl.
*A61K 31/4965* (2006.01)
(52) U.S. Cl. .............. 514/255.05; 544/336; 548/465
(58) Field of Classification Search ............ 514/255.05; 544/336; 548/465
See application file for complete search history.

(56) References Cited

FOREIGN PATENT DOCUMENTS

| WO | WO 02/18369 A2 | 3/2002 |
|---|---|---|
| WO | WO 2005/025517 A2 | 3/2005 |
| WO | WO 2009/055467 | * 4/2009 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, 1, 975-976.*
Lin et al. "In Vitro Resistance Studies of Hepatitis C Virus Serine Protease Inhibitors, VX-950 and BILN 2061," The Journal of Biological Chemistry, 2004, vol. 279, No. 17, pp. 17508-17514.

* cited by examiner

*Primary Examiner* — James O. Wilson
*Assistant Examiner* — Douglas M Willis
(74) *Attorney, Agent, or Firm* — Kilpatrick Townsend & Stockton LLP

(57) ABSTRACT

The present invention is directed to compounds of formula I, below, that have the dual property of acting as cathepsin S inhibitors and of inhibiting HCV replication. Such compounds are therefore useful in treating disease states that include hepatitis C, Alzheimer's disease, and autoimmune disorders. The present invention is also directed to pharmaceutical compositions containing these compounds, and processes for preparing the compounds.

Formula I

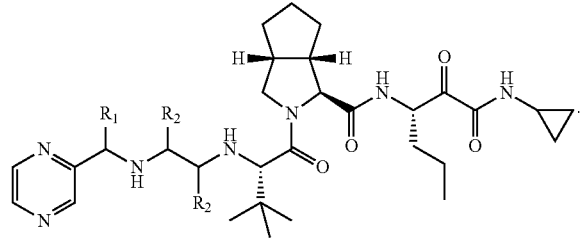

15 Claims, No Drawings

SUBSTITUTED PYRAZINES THAT INHIBIT PROTEASE CATHEPSIN S AND HCV REPLICATION

CROSS-REFERENCES TO RELATED APPLICATIONS

This application claims the benefit of Provisional Application Ser. No. 60/982,278, filed Oct. 24, 2007, and Provisional Application Ser. No. 61/037,656, filed Mar. 18, 2008, each of which is incorporated herein by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is directed to compounds that have the dual property of acting as cathepsin S inhibitors and of inhibiting HCV replication. Such compounds are therefore useful in treating disease states that include hepatitis C, Alzheimer's disease, and autoimmune disorders. The present invention is also directed to pharmaceutical compositions containing these compounds, and processes for preparing the compounds.

STATE OF THE ART

Inhibition of HCV Replication Hepatitis C virus (HCV) is a (+)-sense single-stranded RNA virus that is a major cause of non-A, non-B hepatitis worldwide. A large percentage of people infected with HCV develop chronic liver disease. This chronic hepatitis C infection, in turn, makes them at high risk for developing serious liver diseases such as liver cirrhosis, hepatocellular carcinoma and terminal liver disease leading to death. Currently, hepatitis C infections are treated with either injectable interferon or with pegylated forms of interferon such as PEG-Intron® and Pegasys®, alone or in combination with Ribavirin. These therapies, however, induce severe side effects such as retinopathy, thyroiditis, acute pancreatitis, depression. Therefore, there is a need for a safe, orally-active drug for the treatment of hepatitis C infections. The present invention fulfils this and related needs.

Inhibition of Cathepsin S Cysteine proteases represent a class of peptidases characterized by the presence of a cysteine residue in the catalytic site of the enzyme. Cysteine proteases are associated with the normal degradation and processing of proteins. However, abnormal activity of cysteine proteases, e.g., as a result of increased expression or enhanced activation, has been shown to have pathological consequences. Examples of cysteine proteases are cathepsins B, K, L, and S. In particular, increased cathepsin B levels are found in tumors; thus, suggesting a role for the enzyme in tumor invasion and metastasis. Additionally, abnormal cathepsin B activity is implicated in such disease states as rheumatoid arthritis, osteoarthritis, acute pancreatitis, inflammatory airway disease and bone and joint disorders. The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well. Cathepsin L is implicated in normal lysosomal proteolysis as well as in several disease states, including, but not limited to, metastasis of melanomas.

The normal protease activity of cathepsin S or its increased expression and activity are associated with a wide range of disease states. In particular, cathepsin S is implicated in Alzheimer's disease, and in certain autoimmune disorders, including, but not limited to juvenile onset diabetes, multiple sclerosis, psoriasis, inflammatory bowel disease, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to, asthma; and allogeneic immune responses, including, but not limited to, immune response to therapeutic agents. Altered expression or activity of cathepsin S has also been implicated in atherosclerosis and the rupture of atherosclerotic plaque.

In view of the number of diseases or conditions related to the activity or the increased expression of cathepsin S, compounds that are capable of inhibiting such activity or expression would accordingly be useful as therapeutic agents for the treatment of certain autoimmune disorders, neuropathic pain, Alzheimer's disease, and atherosclerosis.

Accordingly, compounds having the dual activity of cathepsin S inhibition and of inhibiting HCV replication would be useful for the treatment of patients having a disease state such as hepatitis C infection, or certain autoimmune disorders, neuropathic pain, Alzheimer's disease, and atherosclerosis, or any combination of the above disease states.

BRIEF SUMMARY OF THE INVENTION

It is an object of the invention to provide compounds that have the dual property of acting as inhibitors of cysteine protease cathepsin S and of inhibiting HCV replication. Accordingly, in a first aspect, the invention relates to compounds of Formula I:

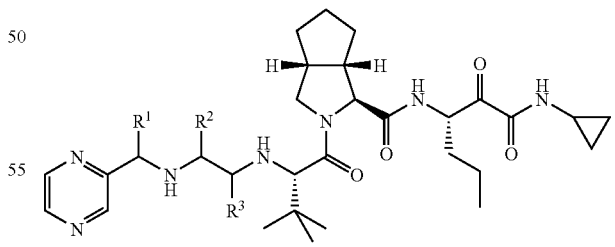

Formula I wherein:
R$^1$ is —CF$_2$X having an absolute stereochemistry of R or S, in which X is selected from the group consisting of hydrogen, fluoro and chloro, or X is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from fluoro and chloro; or R[1] is oxo;

R[2] is selected from the group consisting of alkyl of 1-6 carbon atoms and cycloalkyl of 3-8 carbon atoms, having an absolute stereochemistry of R or S, each of which is optionally substituted by 1, 2 or 3 groups selected from the group consisting of fluoro, chloro, and cycloalkyl of 3-6 carbon atoms, and R[3] is —CF$_2$Y having an absolute stereochemistry of R or S, in which Y is selected from the group consisting of hydrogen, fluoro and chloro, or Y is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from the group consisting of fluoro and chloro; or R[3] is oxo;

with the proviso that R[1] and R[3] are different;

and the pharmaceutically acceptable salts, hydrates, and prodrugs thereof.

In a second aspect, the invention is related to compounds of the formulae IA, IB, IC, ID, IE, and IF:

IA

IB

IC

ID

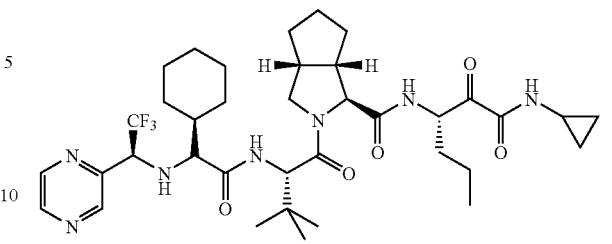

IE

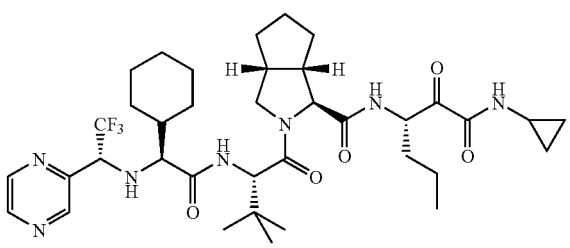

IF

A third aspect of this invention relates to pharmaceutical formulations, comprising a therapeutically effective amount of a compound of Formula I, particularly compounds of formula IA, IB, IC, ID, IE, or IF, or a mixture of one or more compounds of formula IA, IB, IC, ID, IE, or IF, and at least one pharmaceutically acceptable excipient.

In a fourth aspect, this invention is directed to a method for using the compounds of Formula I, particularly the compounds of formula IA, IB, IC, ID, IE, or IF in the treatment of a disease or condition in a mammal that is amenable to treatment with a protease cathepsin S inhibitor or an inhibitor of HCV replication, comprising administering to the mammal a pharmaceutical composition comprising a therapeutically effective amount of a compound of Formula I, particularly a compound of formula IA, IB, IC, ID, IE, or IF, or a mixture of one or more compounds of formula IA, IB, IC, ID, IE, or IF, and/or pharmaceutically acceptable salts thereof, optionally in admixture with one or more pharmaceutically acceptable excipient. Such diseases include, but are not limited to, at least one of hepatitis C, Alzheimer's disease, certain autoimmune disorders, which include, but are not limited to, atherosclerosis, rupture of atherosclerotic plaque, juvenile onset diabetes, multiple sclerosis, psoriasis, inflammatory bowel disease, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in allergic disorders, including, but not limited to, asthma; and allogenic immune responses, including, but not limited to, immunr response to therapeutic agents.

In a fifth aspect, this invention is directed to processes for preparing compounds of Formula I, in particular compounds of formula IA, IB, IC, ID, IE, and IF.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

"Alkyl" represented by itself means a straight or branched, saturated aliphatic radical containing 1, 2, 3, 4, 5, or 6 carbon atoms, unless otherwise indicated e.g., methyl, ethyl, n-propyl, isopropyl, butyl, sec-butyl, isobutyl, tert-butyl, n-pentyl, n-hexyl, and the like.

"Halo" refers to fluoro, chloro, bromo or iodo.

"Optional" or "optionally" means that the subsequently described event or circumstance may or may not occur, and that the description includes instances where said event or circumstance occurs and instances in which it does not.

"Cycloalkyl" refers to a monovalent saturated monocyclic carbon ring containing 3, 4, 5, 6, 7, or 8 ring carbon atoms e.g., cyclopropyl, cyclobutyl, cyclopentyl, cyclohexyl, cycloheptyl, and the like.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog RS system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" or "therapeutically effective dose" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The present invention also includes prodrugs of a compound of Formula I. Prodrug means a compound that is convertible in vivo by metabolic means (e.g. by hydrolysis) to a compound of Formula I. For example, an ester of a compound of Formula I containing a hydroxy group may be convertible by hydrolysis in vivo to the parent molecule. Alternatively an ester of a compound of Formula I containing a carboxy group may be convertible by hydrolysis in vivo to the parent molecule. Suitable esters of compounds of Formula I containing a hydroxy group, are for example acetates, citrates, lactates, tartrates, malonates, oxalates, salicylates, propionates, succinates, fumarates, maleates, methylenebis-βb-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula I containing a carboxy group, are for example those described by Leinweber, F. J. *Drug Metab. Res.*, 1987, 18, page 379. An especially useful class of esters of compounds of Formula I containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates. It is understood that the names and illustration used in this Application to describe compounds of Formula I are meant to be encompassed all possible prodrugs thereof.

"Protected derivatives" means derivatives of compounds of Formula I in which a reactive site or sites are blocked with protecting groups. Protected derivatives of compounds of Formula I are useful in the preparation of compounds of Formula I or in themselves may be useful as cathepsin inhibitors. A comprehensive list of suitable protecting groups can be found in T. W. Greene, *Protective Groups in Organic Synthesis*, 3rd edition, John Wiley & Sons, Inc. 1999. It is understood that the names and illustration used in this Application to describe compounds of Formula I are meant to be encompassed all possible protected derivatives thereof.

Preferred Embodiments

Certain compounds of Formula I within the broadest scope set forth in the Summary of the Invention are preferred. For example:

One preferred group of compounds includes those compounds of Formula I in which $R^1$ is oxo and $R^2$ is cycloalkyl of 3-6 carbon atoms, particularly cyclohexyl. Within this group a preferred subgroup includes those compounds in which $R^3$ is —$CF_2Y$, particularly where Y is hydrogen, fluoro, or chloro, particularly fluoro.

Another preferred group of compounds includes those compounds of Formula I in which $R^1$ is —$CF_2X$, in which X is hydrogen, fluoro, or chloro, particularly fluoro, and $R^3$ is oxo. Within this group a preferred subgroup includes those compounds in which $R^2$ is cycloalkyl of 3-6 carbon atoms, particularly cyclohexyl.

Preferred compounds of the invention are named as follows:

Nomenclature

IA: (1S,3aR,6aS)-2-((S)-2-((2S,3R)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

IB: (1S,3aR,6aS)-2-((S)-2-((2R,3S)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

IC: (1S,3aR,6aS)-2-((S)-2-((2S,3S)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

ID: (1S,3aR,6aS)-2-((S)-2-((2R,3R)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

IE: (1S,3aR,6aS)-2-((S)-2-((S)-(2-cyclohexyl-2-((S)-2,2,2-trifluoro-1-(pyrazin-2-yl)ethylamino)acetamido-3,3-dimethylbutanoyl)-N-((S)-1-(cyclopropylamino)-1,2-dioxohexan-3-yl)octahydrocyclopenta[c]pyrrole-1-carboxamide.

IF: (1S,3aR,6aS)-2-((S)-2-((S)-(2-cyclohexyl-2-((R)-2,2,2-trifluoro-1-(pyrazin-2-yl)ethylamino)acetamido-3,3-dimethylbutanoyl)-N-((S)-1-(cyclopropylamino)-1,2-dioxohexan-3-yl)octahydrocyclopenta[c]pyrrole-1-carboxamide.

The names of the compounds of the invention were generated by ChemBioDraw Ultra, Version 11.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I are prepared through a common intermediate of formula (7), the preparation of which is shown below in Reaction Scheme I.

REACTION SCHEME I

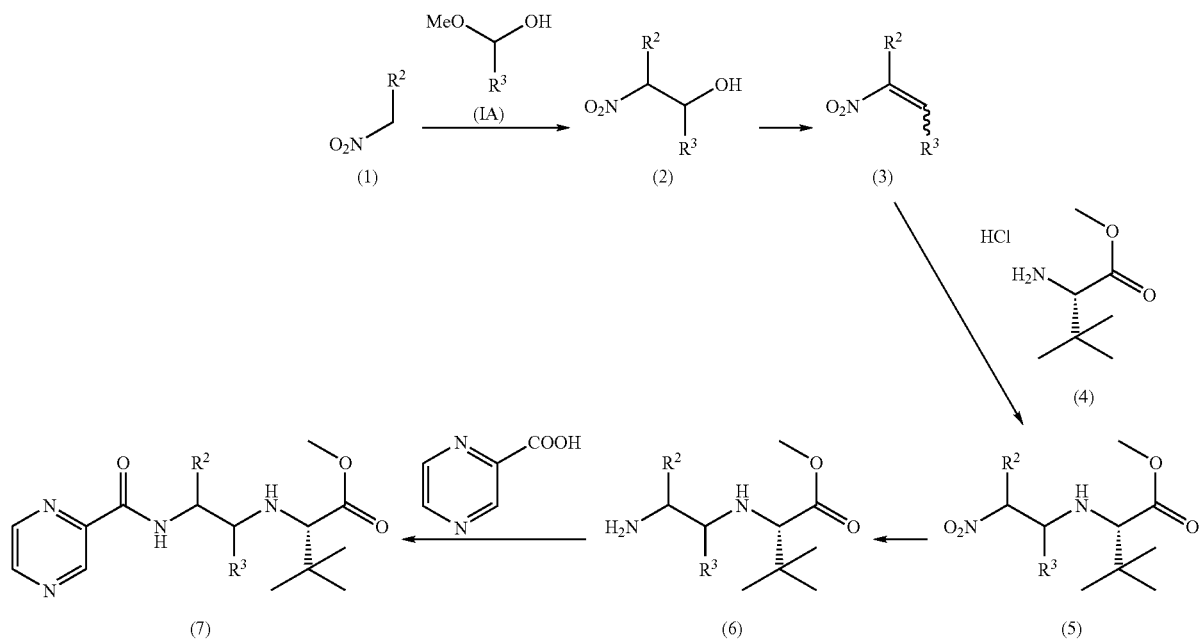

Step 1—Preparation of a Compound of Formula (2)

A mixture of the nitro derivative of formula (2) and the compound of formula (1A) and a base, for example potassium carbonate, is heated to about 60° C. for about 12-24 hours. When the reaction is substantially complete, the product of formula (2) is isolated by conventional means, for example by addition of the mixture to water and extraction of the desired product with an inert organic solvent, which is dried, the solvent removed under reduced pressure, and chromatography of the residue on silica gel to provide the compound of formula (2).

Step 2—Preparation of a Compound of Formula (3)

A mixture of the product from Step 1, the compound of formula (2), and a mild dehydrating reagent, for example ([methoxycarbonylsulfamoyl]triethylammonium hydroxide, inner salt) (Burgess reagent) in an inert organic solvent, for example benzene, is heated to about 70° C. for about 90 minutes. When the reaction is substantially complete, the product of formula (3) is isolated by conventional means, for example by separation of the organic solvent layer, removal of the solvent under reduced pressure, and chromatography of the residue on silica gel.

Step 3—Preparation of a Compound of Formula (5)

A mixture of the compound of formula (3) and (S)-methyl 2-amino-3,3-dimethylbutanoate, the compound of formula (4), in the presence of a hindered tertiary amine, for example diisopropylethylamine, in an inert solvent, for example toluene, is heated to about 100° C. for about 12-30 hours. When the reaction is substantially complete, the product of formula (5) is isolated by conventional means, for example by extraction with an inert organic solvent, separation of the organic solvent layer, removal of the solvent under reduced pressure, to provide the compound of formula (5) as a mixture of isomers, which are separated by chromatography on silica gel into a faster eluting diastereoisomer designated as formula (5A), and a slower eluting diastereoisomer designated as (5B). One of (5A) and (5B) is the 2,3-syn dl pair, and the other the 2,3-anti dl pair, although at this time the absolute assignment of stereochemistry for the two isomers has not been determined. That is, if (5A) is the 2,3-syn dl pair:

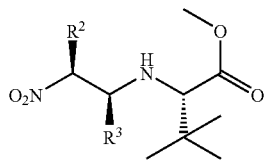

then (5B) is the 2,3-anti dl pair:

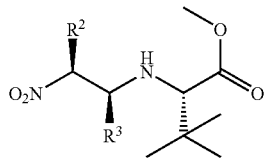

Step 4—Preparation of a Compound of Formula (6)

One of the diastereoisomeric pairs separated above, for example (5A), in a protic solvent, for example ethanol, is hydrogenated in the presence of a hydrogenation catalyst, for example Raney Nickel catalyst, under pressure, for example at 50 psi for 12-24 hours. When the reaction is substantially complete, the product of formula (6) is isolated by conventional means, for example by removal of the catalyst, evaporation of the solvent under reduced pressure, to provide a compound of formula (6), designated as (6A), which is either the 2,3-syn dl pair isomer or the 2,3-anti dl pair. Chromatography of (6A) on silica gel provides two pure isomers, a faster eluting compound designated as 6A-Isomer A and a slower eluting compound designated as 6A-Isomer B. At this time the absolute assignment of stereochemistry of these two isomers has not been determined, but NMR shows that they are either the 2,3-syn dl pair isomer or the 2,3-anti dl pair isomer. That is, if (5A) is the 2,3-syn dl pair isomer, then 6A-isomer A is either:

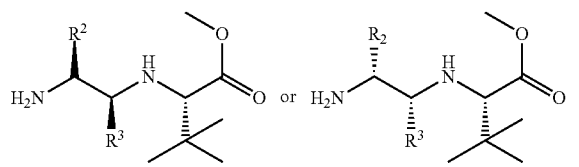

and 6A-isomer B is the other stereoisomer.

Similarly, starting with the compound designated as (5B), and carrying out the procedure detailed in step 4, silica gel chromatography of the product provides two pure stereoisomers designated as 6B-isomer A and 6B-isomer B. That is, if 5B is the 2,3-anti dl pair isomer, then 6B-isomer A is either:

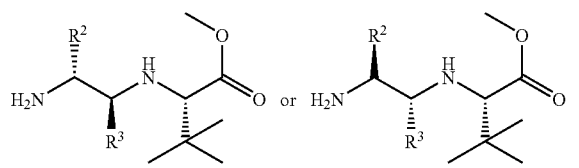

and 6B-isomer B is the other stereoisomer.

Step 5—Preparation of a Compound of Formula (7)

The compound designated as 6A-Isomer A, is contacted with pyrazinecarboxylic acid in the presence of reagents suitable for amide formation, for example 1-ethyl-3-(3'-dimethylaminopropyl)carbodiimide (EDCI) and 1-hydroxybenzotriazole (HOBT), in the presence of a mild base, for example N-methylmorpholine NMM, in an inert organic solvent, for example dichloromethane. The reaction is conducted at about room temperature, for about 24 hours. When the reaction is substantially complete, the product of formula (7) is isolated by conventional means, for example by diluting the reaction mixture with an inert organic solvent, for example ethyl acetate, and washing with dilute hydrochloric acid, water, brine and drying. Removal of the solvent under reduced pressure provides a stereoisomer designated as 7A-isomer A.

Similarly, starting with the compound identified as 6A-isomer B, and carrying out the procedure detailed in step 5, a stereoisomer designated as 7A-isomer B is obtained.

Similarly, starting with the compound identified as 6B-isomer A, and carrying out the procedure detailed in step 5, a stereoisomer designated as 7B-isomer A is obtained.

Similarly, starting with the compound identified as 6B-isomer B, and carrying out the procedure detailed in step 5, a stereoisomer designated as 7B-isomer B is obtained.

Similarly, other stereoisomers of formula (7) are obtained.

Alternative Preparation of a Compound of Formula (7)

Alternatively, the mixture of stereoisomers of the nitro compound of formula (5A) can be hydrogenated with Raney Nickel Catalyst as shown above, and the crude product of formula (6A) reacted with no further separation with pyrazinecarboxylic acid as described in step 5 above. The product thus obtained is a mixture of two diastereoisomers, ((RR,SS) or (RS,SR)), and is chromatographed, for example on silica gel, to provide two separate stereoisomers, designated as 7A-isomer A (the faster eluting isomer) and 7A-isomer B (the slower eluting isomer).

Similarly, starting with the stereoisomers of the nitro compound of formula (5B) and following the above procedure, two separate diastereoisomers, designated as 7B-isomer A and 7B-isomer B, are obtained.

The stereoisomer 7A-isomer A, 7A-isomer B, 7B-isomer A, or 7B-isomer B, prepared by the method of Reaction Scheme I or the alternative method of preparation of a compound of formula (7) described above, is then converted to the corresponding stereoisomer of formula (10), as shown below in Reaction Scheme II.

REACTION SCHEME II

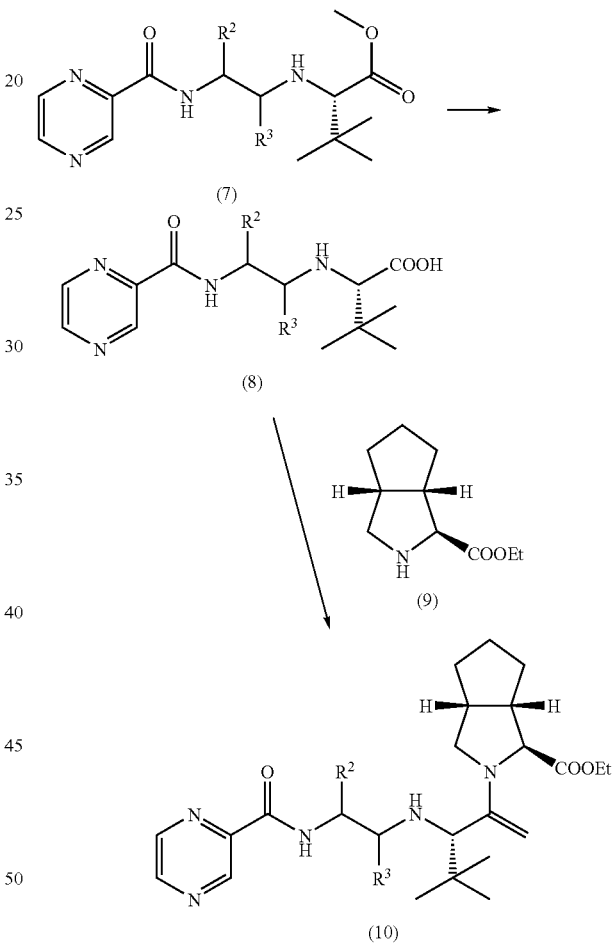

Step 1—Preparation of a Compound of Formula (8)

The stereoisomer designated as 7A-isomer A, for example, is reacted with an agent capable of mild hydrolysis of the methyl ester group, for example potassium trimethylsilanolate. The reaction is conducted in an inert organic solvent, for example tetrahydrofuran, in a microwave apparatus at about 140° C. for about 10 minutes. When the reaction is substantially complete, the product of formula (8) is isolated by conventional means, for example by diluting the reaction mixture with an inert organic solvent, for example ethyl acetate, and washing with dilute hydrochloric acid, water, brine and drying. Removal of the solvent under reduced pressure provides a stereoisomer of a compound of formula (8), designated as 8A-isomer A.

Similarly, starting with the diastereoisomer designated as 7A-isomer B, and following the procedure of Reaction Scheme II, Step 1, a stereoisomer of a compound of formula (8), designated as 8A-isomer B, is obtained.

Similarly, starting with the diastereoisomer designated as 7B-isomer A, and following the procedure of Reaction Scheme II, Step 1, a stereoisomer of a compound of formula (8), designated as 8B-isomer A, is obtained.

Similarly, starting with the stereoisomer designated as 7B-isomer B, and following the procedure of Reaction Scheme II, Step 1, a stereoisomer of a compound of formula (8), designated as 8B-isomer B, is obtained.

Step 2—Preparation of a compound of Formula (10)

The stereoisomer designated as 8A-isomer A, for example, is reacted with (1S,3aR,6aS)-ethyl octahydrocyclopenta[c]pyrrole-1-carboxylate (the compound of formula (9), prepared as shown in Preparation 2 below) in the presence of a mild base, for example N-methylmorpholine, and O-(7-azabenzotriazole-1-yl)-N,N,N',N'-tetramethyluronium hexafluorophosphate (HATU) in an inert organic solvent or mixtures of inert organic solvents, for example N,N-dimethylformamide and tetrahydrofuran. The reaction is conducted at a temperature of about room temperature, for about 12-24 hours. When the reaction is substantially complete, the product is isolated by conventional means, for example by diluting the reaction mixture with an inert organic solvent, for example ethyl acetate, and washing with dilute hydrochloric acid, water, brine and drying. Removal of the solvent under reduced pressure provides a diastereoisomer of a compound of formula (10), designated as 10A-isomer A.

Similarly, starting with the stereoisomer designated as 8A-isomer B, and following the procedure of Reaction Scheme II, Step 2, a stereoisomer of a compound of formula (10), designated as 10A-isomer B, is obtained.

Similarly, starting with the stereoisomer designated as 8B-isomer A, and following the procedure of Reaction Scheme II, Step 2, a stereoisomer of a compound of formula (10), designated as 10B-isomer A, is obtained.

Similarly, starting with the stereoisomer designated as 8B-isomer B, and following the procedure of Reaction Scheme II, Step 2, a stereoisomer of a compound of formula (10), designated as 10B-isomer B, is obtained.

The stereoisomers designated as 10A-isomer A, 10A-isomer B, 10B-isomer A, and 10B-isomer B are then converted to a stereoisomer of a compound of Formula I, designated as IA, IB, IC, and ID, as shown in Reaction Scheme III.

REACTION SCHEME III

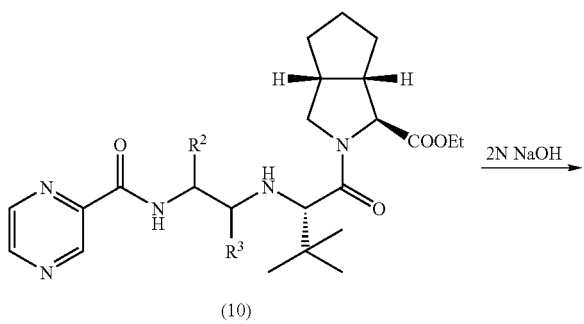

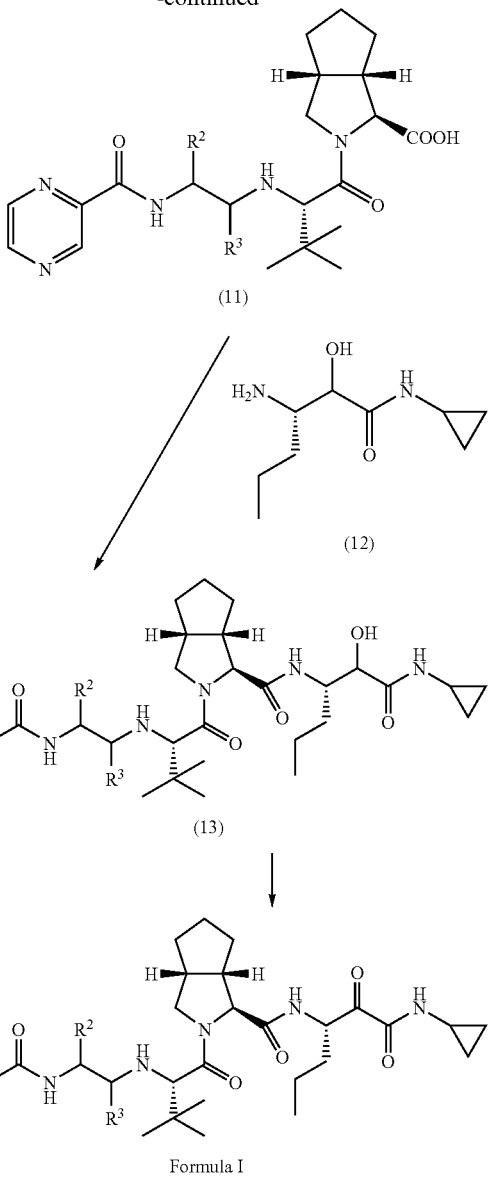

Step 1—Preparation of a Compound of Formula (11)

One of the stereoisomers of a compound of formula (10), for example 10A-isomer A, is hydrolyzed to the equivalent carboxylic acid of formula (11) by reaction with an aqueous base, for example aqueous sodium hydroxide solution, in a protic solvent, for example ethanol. The reaction is conducted at a temperature of about 50-75° C. for about 1-3 hours. When the reaction is substantially complete, the stereoisomer of formula (11) is isolated by conventional means, for example by diluting the reaction mixture with an inert organic solvent, for example ethyl acetate, and washing with dilute hydrochloric acid, water, brine and drying. Removal of the solvent under reduced pressure provides a stereoisomer of a compound of formula (11), designated as 11A-isomer A.

Similarly, starting with a stereoisomer of formula 10A-isomer B, 10B-isomer A, or 10B-isomer B, the corresponding stereoisomers of formula 11A-isomer B, 11B-isomer A and 11B-isomer B are obtained.

Step 2—Preparation of a Compound of Formula (13)

A stereoisomer of a compound of formula (11), for example formula 11A-isomer A, is reacted with (3S)-3- amino-N-cyclopropyl-2-hydroxyhexanamide hydrochloride (the compound of formula (12), prepared as described in Preparation 1 below) in the presence of reagents suitable for amide formation, for example 1-ethyl-3-(3'-dimethylaminopropyl)carbodiimide (EDCI) and 1-hydroxybenzotriazole (HOBT), in the presence of a mild base, for example N-methylmorpholine (NMM), in an inert organic solvent or solvents, for example a mixture of tetrahydrofuran and dichloromethane. The reaction is conducted at a temperature of about room temperature for about 12-24 hours. When the reaction is substantially complete, the equivalent stereoisomer of formula (13) is isolated by conventional means, for example by diluting the reaction mixture with an inert organic solvent, for example ethyl acetate, and washing with dilute hydrochloric acid, water, brine and drying. Removal of the solvent under reduced pressure provides a stereoisomer of a compound of formula (13), designated as 13A-isomer A, which may be used in the next reaction without purification.

Similarly, starting with a stereoisomer of formula 11A-isomer B, 11B-isomer A, or 11B-isomer B, the corresponding stereoisomers of formula 13A-isomer B, 13B-isomer A, or 13B-isomer B are obtained.

Step 3—Preparation of a Compound of Formula I in which $R^1$ is Oxo

A stereoisomer selected from 13A-isomer A, 13A-isomer B, 13B-isomer A, or 13B-isomer B, for example 13A-isomer A, is reacted with a mild oxidizing agent, for example 1,1,1-triacetoxy-1,1-dihydro-1,2-benziodoxol-3(1H)-one (Dess Martin periodinanane Reagent). The reaction is conducted in an inert organic solvent, for example dichloromethane, for about 1 hour at about room temperature. When the reaction is substantially complete, the product of Formula I is isolated by conventional means, for example by diluting the reaction mixture with an inert organic solvent, for example ethyl acetate, and washing with dilute sodium bicarbonate, water, brine and drying. Removal of the solvent under reduced pressure provides a crude product of Formula I, which may be purified by silica gel column chromatography, to provide a pure compound designated as Formula I isomer A. Similarly, starting with stereoisomer 13A-isomer B, 13B-isomer A, or 13B-isomer B, the corresponding compounds of Formula I isomer B, Formula I isomer C, or Formula I isomer D are obtained. The compounds of Formula I isomer A, Formula I isomer B, Formula I isomer C, or Formula I isomer D where $R^2$ is cyclohexyl and $R^3$ is trifluoromethyl correspond to the compounds shown as Formula IA, IB, IC, and ID, but the absolute assignment of stereochemistry has not yet been established. That is, the absolute stereochemistry of the compound shown as Formula IA is not necessarily that shown for Formula I isomer A, the compound of Formula IB does not necessarily correspond to Formula I isomer B, etc.

Synthesis of the Compounds of Formula IE and IF

The compounds of Formula I in which $R^1$ is trifluoromethyl are prepared by reaction of two intermediates, compounds (17) and (21), the preparation of which is shown below in Reaction Schemes IV and V.

A. Preparation of Intermediate (17)

REACTION SCHEME IV

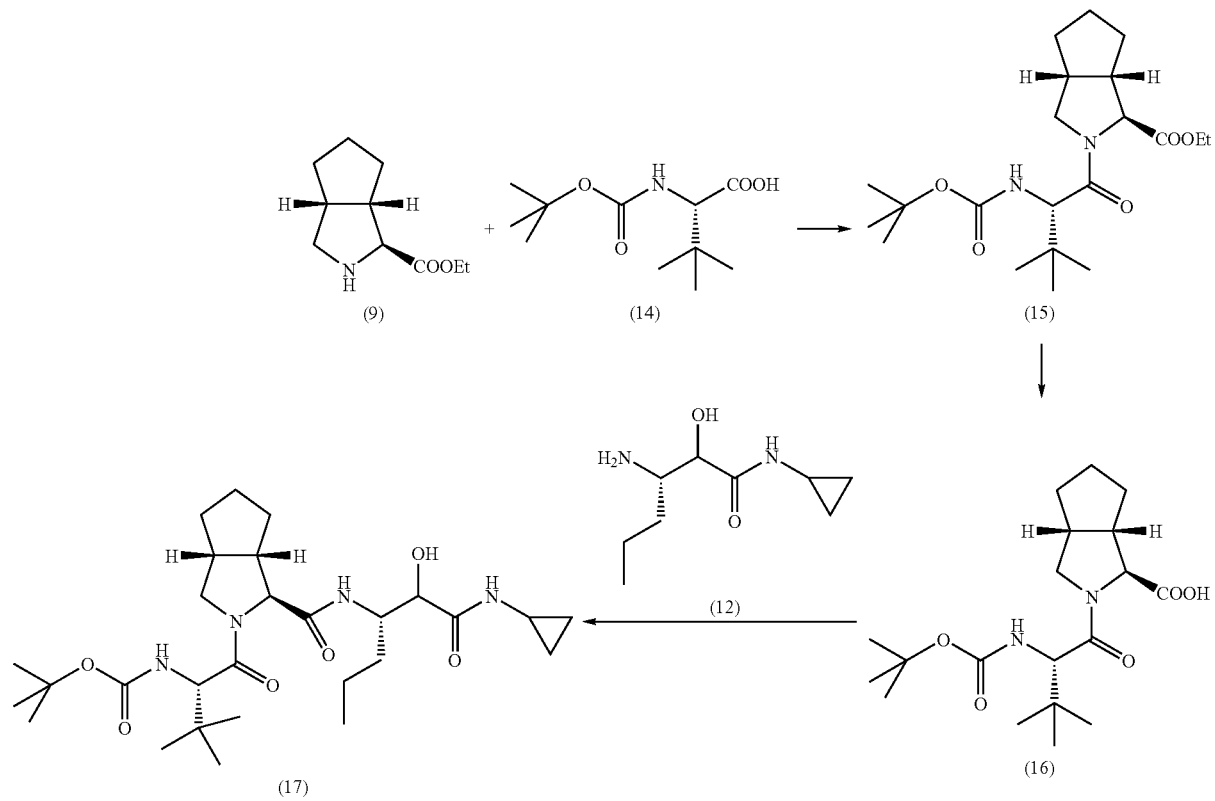

Step 1—Preparation of a Compound of Formula (15)

(1S,3aR,6aS)-ethyl octahydrocyclopenta[c]pyrrole-1-carboxylate (the compound of formula (9) as the free base), prepared as shown in Preparation 2 below), is reacted with L-N-Boc-tert-butylglycine in the presence of in the presence of reagents suitable for amide formation, for example N,N'-dicyclohexylcarbodiimide (DCC) and 1-hydroxybenzotriazole (HOBT), in an inert organic solvent or solvents, for example a mixture of tetrahydrofuran and dichloromethane, optionally in the presence of a tertiary base. The reaction is conducted at a temperature of about room temperature for about 12-24 hours. When the reaction is substantially complete, the compound of formula (15) is isolated by conventional means, for example by diluting the reaction mixture with an inert organic solvent, for example dichloromethane, filtering, and removing the solvent under reduced pressure, to provide crude (15), (1S,3aR,6aS)-ethyl-2-((S)-2-(tert-butoxycarbonylamino)-3,3-dimethylbutanoyl)octahydrocyclopenta-[c]pyrrole-1-carboxylate, which may be used in the next reaction without purification.

Step 2—Preparation of a Compound of Formula (16)

The crude product from step 1 is dissolved in a protic solvent, for example methanol, and reacted with an aqueous base, for example aqueous sodium hydroxide solution. The reaction is conducted at a temperature of about room temperature for about 30 minutes. When the reaction is substantially complete, the compound of formula (16) is isolated by conventional means, for example by acidification with a strong acid, for example aqueous hydrochloric acid, and extracting the product into an inert solvent, for example ethyl acetate, which is washed with dilute hydrochloric acid, water, brine and drying. Removal of the solvent under reduced pressure provides a compound of formula (16), (1S,3aR,6aS)-2-((S)-2-(tert-butoxycarbonylamino)-3,3-dimethylbutanoyl)-octahydrocyclopenta[c]pyrrole-1-carboxylic acid, which may be used in the next reaction without purification.

Step 3—Preparation of a Compound of Formula (17)

The crude product from step 2 is dissolved in an inert solvent, for example dichloromethane, and treated with reagents suitable for amide formation, for example 1-ethyl-3-(3'-dimethylaminopropyl)carbodiimide (EDCI) and 1-hydroxybenzotriazole (HOBT), in the presence of a mild base, for example N-methylmorpholine (NMM). To this mixture is added 3-amino-N-cyclopropyl-2-hydroxyhexanamide (12) in an inert solvent, for example dichloromethane, or a mixture of inert solvents, for example dichloromethane and N,N-dimethylformamide. The reaction is conducted at a temperature of about room temperature for about 12-24 hours. When the reaction is substantially complete, the compound of formula (17) is isolated by conventional means, for example by diluting with water, extracting the product into an inert solvent, for example ethyl acetate, washing with brine and drying. Removal of the solvent under reduced pressure provides a compound of formula (17), tert-butyl (2S)-2-((S,3aR,6aS)-1-((3S)-1-(cyclopropylamino)-2-hydroxy-1-oxohexan-3-yl-carbamoyl)-hexahydrocyclopenta[c]pyrrol-2(1H)-yl)-3,3-dimethyl-1-oxobutan-2-ylcarbamate.

B Preparation of Intermediate (21)

REACTION SCHEME V

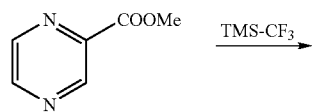

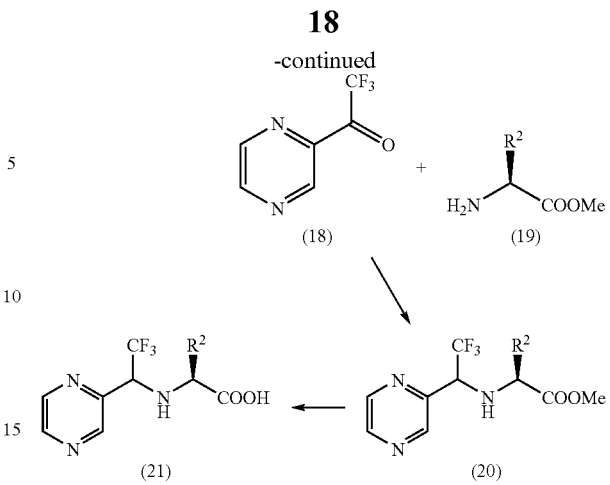

Step 1—Preparation of a Compound of Formula (18)

A solution of pyrazine carboxylate methyl ester is dissolved in an inert solvent, for example monoglyme (dimethoxyethane). To this solution is added a mixture of trimethylsilyltrifluoromethane and dry caesium fluoride. After about 12-24 hours, at a temperature of about room temperature, the solvent is removed under reduced pressure. The residue is dissolved in a mixture of an inert solvent, for example tetrahydrofuran, and an organic acid, for example acetic acid, and the mixture is treated with tert-butylammonium fluoride. The reaction is conducted at a temperature of about room temperature for about 3 hours. When the reaction is substantially complete, the compound of formula (18) is isolated by conventional means, for example by diluting with water, extracting the product into an inert solvent, for example ethyl acetate, washing with a solution of a mild inorganic base, for example sodium bicarbonate, and drying. Removal of the solvent under reduced pressure provides a crude compound, which can be purified by trituration with an inert solvent, for example a mixture of dichloromethane and hexane, to give a compound of formula (18), 2,2,2-trifluoro-1-(pyrazin-2-yl)ethanone.

Compounds of formula (18) where $R^1$ is other than trifluoromethyl are prepared in a similar manner, starting with the appropriate trimethylsilyl reagent.

Step 2—Preparation of a Compound of Formula (20)

The product of step 1 is dissolved in an inert solvent, for example N,N-dimethylformamide, or a mixture of N,N-dimethylformamide and tetrahydrofuran, a compound of formula (19), optionally as a hydrochloride salt, and a hindered organic base, for example diisopropylethylamine added. To this mixture is slowly added a solution of titanium tetrachloride in dichloromethane. The reaction is conducted at a temperature of about room temperature for about 18-24 hours, after which a further portion of titanium tetrachloride in dichloromethane may be optionally added. When the reaction is substantially complete, a solution of the product is obtained as a mixture of geometric stereoisomers.

To this solution, a solution of sodium cyanoborohydride (NaCNBH$_4$) in a protic solvent, for example methanol, is added slowly. The reaction is conducted at a temperature of about room temperature, for about 2-4 hours, after which the reaction mixture is diluted with an inert solvent, for example ethyl acetate, and dried over magnesium sulfate. Removal of the solvent under reduced pressure provides a crude compound of formula (20), which is a mixture of stereoisomers. Chromatography over silica gel provides a faster eluting band, which is designated as 20-Isomer A, and a slower eluting band, which is designated as 20-Isomer B. At this time the absolute assignment of stereochemistry for the two stereoisomers has not been determined.

Step 3—Preparation of a Compound of Formula (21)

One of the two stereoisomers separated in step 2, for example 20-isomer A, is dissolved in an inert solvent, for example carbon tetrachloride, and cooled to about 0° C. To this solution is added trimethylsilyliodide, and the reaction mixture heated to about 50° C. for about 24-72 hours. When the reaction is substantially complete, the compound of formula (21) is isolated by conventional means, for example adding an inert solvent, for example dichloromethane, washing the mixture with an aqueous solution of sodium thiosulfate ($Na_2S_2O_3$), brine, dried over anhydrous magnesium sulfate and removing the solvent under reduced pressure, to give a stereoisomer designated as 21-Isomer A.

Similarly, starting with the other stereoisomer, 20-isomer B, and following the above procedure, a compound designated as 21-Isomer B is obtained.

The intermediates of formula (17) and 21-Isomer A or 21-Isomer B are then used to provide a compound of Formula I, as shown in Reaction Scheme VI.

Step 2—Preparation of a Compound of Formula (23)

The compound of formula (22), obtained from step 1, is dissolved in an inert solvent, or mixture of inert solvents, for example dichloromethane and N,N-dimethylformamide. To this solution is added one of the stereoisomers obtained in Reaction Scheme V, step 3, for example 21-Isomer A, and reagents suitable for amide formation, for example 1-ethyl-3-(3'-dimethylaminopropyl)carbodiimide (EDCI) and 1-hydroxybenzotriazole (HOBT), in the presence of a mild base, for example N-methylmorpholine (NMM). The reaction is conducted at about room temperature for about 12-24 hours. When the reaction is substantially complete, the compound of formula (23) is isolated by conventional means, for example addition of an inert solvent, for example ethyl acetate, then wash with aqueous hydrochloric acid, dilute aqueous sodium bicarbonate solution, brine, and drying over anhydrous sodium sulfate. The solvent is removed under reduced pressure, to provide a stereoisomer of a compound of formula (23), designated as 23-Isomer-A. The absolute stereochemistry has not yet been established.

REACTION SCHEME VI

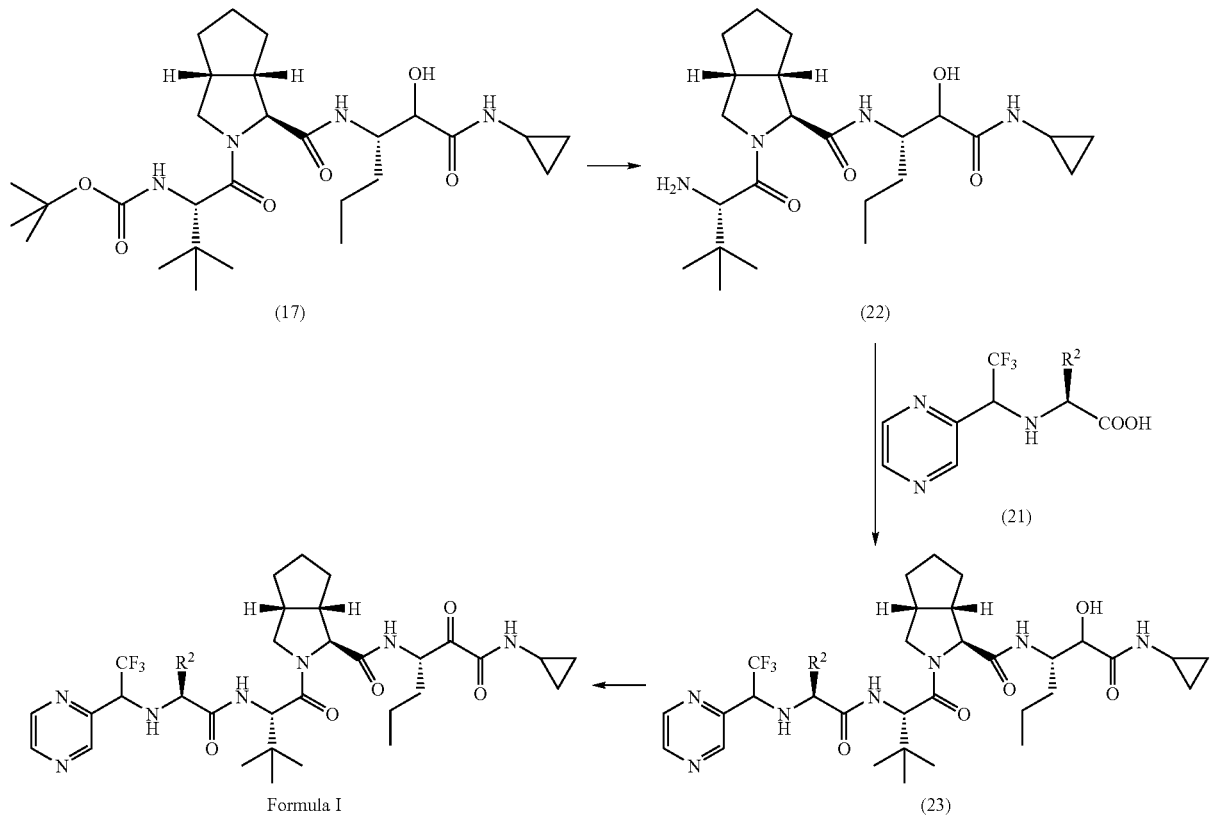

Step 1—Preparation of a Compound of Formula (22)

The compound of formula (17), prepared as shown in Reaction Scheme IV, step 3, is dissolved in an inert solvent, for example dichloromethane. To this solution at about room temperature is added a strong organic acid, for example trifluoroacetic acid. After about 1 hour, an inert solvent is added, for example toluene, and the solvent removed under reduced pressure, to provide a compound of formula (22), which can be used in the next reaction without further purification.

Similarly, replacing 21-Isomer A with 21-Isomer B, and following the procedure of step 2, the other stereoisomer of the compound of formula (23) is obtained, designated as 23-Isomer-B.

Step 3—Preparation of a Compound of Formula I

One of the stereoisomers obtained in step 2, for example 23-Isomer-A, is reacted with a mild oxidizing agent, for example 1,1,1-triacetoxy-1,1-dihydro-1,2-benziodoxol-3 (1H)one (Dess Martin periodinanane Reagent). The reaction is conducted in an inert organic solvent, for example dichloromethane, for about 1-6 hours at about room temperature. When the reaction is substantially complete, the product of Formula I is isolated by conventional means, for example by diluting the reaction mixture with an inert organic solvent, for example ethyl acetate, and washing with dilute sodium bicarbonate, water, brine and drying. Removal of the solvent under reduced pressure provides a crude product, purification of which with reverse phase chromatography provides a pure compound designated as Formula I isomer E. However, the absolute stereochemistry of these stereoisomers has not yet been established at this time.

Similarly, starting with 23-Isomer B, the other stereoisomer of formula IE or IF is obtained, designated as Formula I isomer F.

General Utility

The compounds of Formula I are effective in the treatment of HCV, and of conditions that respond to administration of cathepsin S inhibitors. Such conditions include, but are not limited to, at least one of hepatitis C, atherosclerosis, Alzheimer's disease, certain autoimmune disorders, which include, but are not limited to, juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to, asthma; and allogeneic immune responses, including, but not limited to, immune response to therapeutic agents.

Testing

Activity testing is conducted as described in those patents and patent applications referenced above, and in the Examples below, and by methods apparent to one skilled in the art.

Administration and Pharmaceutical Compositions

In general, compounds of Formula I will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula I may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula I for treating a given disease.

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolution systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Additionally, compounds of the invention may be physically combined with conventional therapeutics or other adjuvants into a single pharmaceutical composition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The present invention is further exemplified, but not limited by, the following preparations and examples that illustrate the preparation of intermediates and compounds of Formula I according to the invention.

Preparation 1

Preparation of (3S)-3-amino-N-cyclopropyl-2-hydroxyhexanamide hydrochloride, the compound of Formula (12)

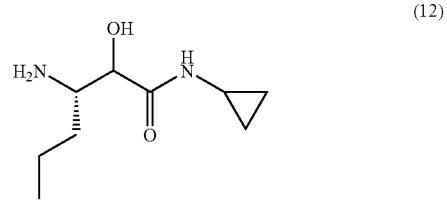

Step 1

To a mixture of Boc-NVa-OH (25 g, 0.115 mol), N,O-dimethylhydroxyamine hydrochloride (12.34 g, 0.127 mol), 1-ethyl-3-(3'-dimethylaminopropyl)carbodiimide (33.07 g, 0.173 mol) and 1-hydroxybenzotriazole (22.9 g, 0.15 mol) in dichloromethane (300 mL), was slowly added N-methylmorpholine (34.9 g, 0.35 mol) under stirring over a 30 minute period. The reaction was stirred at room temperature for 2 hours, then diluted with 2000 mL ethyl acetate, washed with a saturated aqueous solution of sodium bicarbonate, water, and brine, and dried over magnesium sulfate. The solvent was removed under reduced pressure to provide [1S-(methoxymethylcarbamoyl)butyl]carbamic acid tert-butyl ester (20 g) as a colorless oil.

Step 2

To a solution of [1S-(methoxymethylcarbamoyl)butyl]carbamic acid tert-butyl ester (7.2 g, 27.7 mmol) in anhydrous tetrahydrofuran (100 mL) under argon at −78° C., was slowly added lithium aluminum hydride (1M in THF, 27.7 mL). After 2 hours the reaction mixture was quenched by slowly adding 1N hydrochloric acid (20 mL) and then allowed to warm up to room temperature. The reaction mixture was diluted with ethyl acetate (600 mL), washed with 1N hydrochloric acid, water, and brine, and dried over magnesium sulfate. Removal of the solvents under reduced pressure provided (1S-formylbutyl)carbamic acid tert-butyl ester (4.8 g) as an oil.

Step 3

To a solution of cyclopropylisonitrile (1.91 g, 28.5 mmol) and (1S-formylbutyl)carbamic acid tert-butyl ester (3.8 g, 19 mmol) in methylene chloride (100 mL) was added acetic acid (2.28 g, 38 mmol) at 0° C. After the addition was complete the reaction mixture was allowed to warm to 25° C. and stirred for 6 hours. The reaction mixture was diluted with ethyl acetate (200 mL), then washed with a saturated aqueous solution of sodium bicarbonate and brine (30 mL) and dried over magnesium sulfate. The solvent was removed under reduced pressure, and the crude product crystallized from 50 mL of ethyl acetate/hexane (v/v=1/1) to give acetic acid 2-tert-butoxycarbonylamino-1-cyclopropylcarbamoylpentyl ester (4.8 g) as a white solid.

Step 4

Into a solution of acetic acid 2-tert-butoxycarbonylamino-1-cyclopropylcarbamoylpentyl ester (4.8 g, 14.6 mmol) in methanol (50 mL) was added aqueous sodium hydroxide solution (1N, 22 mL) at room temperature. After 2 hours, the methanol was removed under reduced pressure and the concentrate extracted with ethyl acetate (300 mL). The ethyl acetate layer was washed with brine and dried over magnesium sulfate. After removal of the solvent under reduced pressure, the crude product was crystallized from 100 mL of ethyl acetate/hexane (v/v=3/1) to give [1S-(cyclopropylcarbamoylhydroxymethyl)butyl]carbamic acid tert-butyl ester (3.5 g) as a white solid.

Step 5

The [1S-(cyclopropylcarbamoylhydroxymethyl)butyl]carbamic acid tert-butyl ester from Step 4 was treated with anhydrous 4N hydrochloric acid/dioxane for 1 hour at room temperature, and the solvent removed under reduced pressure, to provide (3S)-3-amino-N-cyclopropyl-2-hydroxyhexanamide hydrochloride, the compound of formula (12) as a white solid.

Preparation 2

Preparation of (1S,3aR,6aS)-ethyl octahydrocyclopenta[c]pyrrole-1-carboxylate hydrochloride, the Compound of Formula (9)

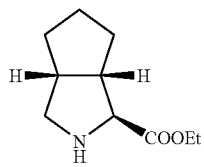

(9)

Step 1

A solution of benzylamine (6.4 mL) and tetrahydro-1H-cyclopenta[c]furan-1,3(3aH)-dione (8 gm) in tetrahydrofuran (28 mL) was heated under reflux for 18 hours. After cooling to room temperature, the reaction mixture was diluted with ethyl acetate, and filtered through a pad of celite. Evaporation under reduced pressure gave crude (3aR,6aS)-2-benzyltetrahydrocyclopenta[c]pyrrole-1,3(2H,3 aH)-dione.

Step 2

The product from step 1 was dissolved in tetrahydrofuran and added to a 1M solution of lithium aluminum hydride in tetrahydrofuran at 0° C. The mixture was refluxed for 18 hours, then cooled to 0° C., and the excess lithium aluminum hydride quenched by cautious addition of water. Filtration through a pad of celite and evaporation of the filtrate under reduced pressure gave crude product, (3aR,6aS)-2-benzyl.octahydrocyclopenta[c]pyrrole.

Step 3

The material from Step 2 was dissolved in ethanol (25 mL) and hydrogenated over 10% Pd on carbon (1.2 gm) for 18 hours at atmospheric pressure. The mixture was filtered through a pad of celite, acidified with 1N hydrochloric acid, and evaporated to dryness under reduced pressure. This product was taken up into dichloromethane (150 mL) and treated successively with di-tert-butyl dicarbonate (12.5 gm, 1.2 eq), dimethylaminopyridine (40 mgm) and triethylamine (17.5 mL, 2.2 eq) at 0° C. After two hours at 0° C. the reaction mixture was diluted with ethyl acetate, and washed successively with 1N hydrochloric acid, water, brine, and then dried over anhydrous sodium sulfate. Evaporation of the organic layer under reduced pressure gave crude product, which was purified by silica gel chromatography, eluting with 5% ethyl acetate/hexane, to provide N-tert-butyloxycarbonyl-octahydrocyclopenta-[c]pyrrole (7.69 gm).

Step 4

Sec-butyl lithium (26.8 mL of a 1.4M solution in cyclohexane; 1.2 eq) was added dropwise to a solution of N-tert-butyloxycarbonyl-octahydrocyclopenta[c]pyrrole (6.6 gm) and tetramethylethylenediamine (TMEDA) (4.69 mL, 1 eq) in diethyl ether (63 mL) at −78° C., and allowed to stir for 1.5 hours. Ethylchloroformate (6 mL, 2 eq) in diethylether (10 mL) was added dropwise to the reaction mixture (maintaining the temperature at −78° C.), and the reaction mixture was allowed to rise to room temperature over a period of 2.5 hours. The temperature was then reduced to −78° C., and quenched by careful addition of hydrochloric acid in tetrahydrofuran (2.2 eq). The reaction was then diluted with ethyl acetate, and washed successively with 1N hydrochloric acid, water, brine, and then dried over anhydrous sodium sulfate. Evaporation of the organic layer under reduced pressure gave crude product, which was purified by column chromatography on silica gel, eluting with 9% ethyl acetate/hexane, to give 2-tert-butyl 1-ethyl hexahydrocyclopenta[c]pyrrole-1,2(1H)-dicarboxylate (2.5 gm).

Step 5

The product of Step 4, 2-tert-butyl 1-ethyl hexahydrocyclopenta[c]pyrrole-1,2(1H)-dicarboxylate, was dissolved in anhydrous 4N hydrochloric acid/dioxane for 1 hour at room temperature, and the solvent removed under reduced pressure, to provide racemic (1S,3aR,6aS)-ethyl octahydrocyclopenta[c]pyrrole-1-carboxylate hydrochloride as a white solid.

It should be noted that 9[(1S,3aR,6aS)-ethyl octahydrocyclopenta[c]pyrrole-1-carboxylate] as a single enantiomer was prepared as described in WO 02/18369, the entire contents of which are hereby incorporated by reference.

Example 1

Preparation of a Compound of Formula (2) in which $R^2$ is Cyclohexyl and $R^3$ is Trifluoromethyl Preparation of 3-cyclohexyl-1,1,1-trifluoro-3-nitropropan-2-ol

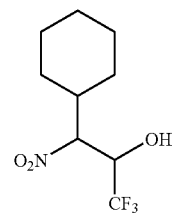

(2)

A mixture of (nitromethyl)cyclohexane (1.15 gm), (R,S)-2,2,2-trifluoro-1-methoxyethanol (1.26 mL) and potassium carbonate (0.76 gm) was heated to 60° C. After 17 hours at 60° C., the reaction mixture was poured into water and the product extracted into diethyl ether (three portions). The combined organic portions were washed with water, brine and then dried over anhydrous sodium sulfate. Evaporation to dryness under reduced pressure gave the crude product, which was purified by silica gel chromatography, eluting with 7% ethyl acetate/hexane, to provide 3-cyclohexyl-1,1,1-trifluoro-3-nitropropan-2-ol, the compound of formula (2), (1.26 gm, 65%).

Example 2

Preparation of a Compound of Formula (3) in which R² is Cyclohexyl and R³ is Trifluoromethyl Preparation of the E- and Z-isomers of (3,3,3-trifluoro-1-nitroprop-1-enyl)cyclohexane

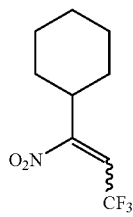

(3)

A mixture of 3-cyclohexyl-1,1,1-trifluoro-3-nitropropan-2-ol (2) (1.015 gm) and ([methoxycarbonylsulfamoyl]triethylammonium hydroxide, inner salt) (Burgess reagent) (2.2 gm) in benzene (10 mL) was heated to 70° C. for 1.5 hours. After cooling the reaction mixture to room temperature, the organic layer was decanted away from the solids and evaporated to dryness under reduced pressure. Purification of the crude product on silica gel chromatography (eluting with 2% ethyl acetate/hexane) gave (3,3,3-trifluoro-1-nitroprop-1-enyl)cyclohexane (0.62 gm, 66%).

Example 3

Preparation of a Compound of Formula (5) in which R² is Cyclohexyl and R³ is Trifluoromethyl Preparation of methyl 2-(3-cyclohexyl-1,1'-trifluoro-3-nitropropan-2-ylamino)-3,3-dimethylbutanoate

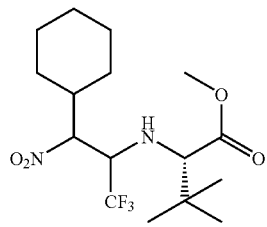

(5)

A mixture of (3,3,3-trifluoro-1-nitroprop-1-enyl)cyclohexane (3) (0.62 gm), (S)-methyl 2-amino-3,3-dimethylbutanoate (4) (0.656 gm, 1.3 eq) and diisopropylethylamine (0.69 mL) in toluene (15 mL) was heated to 100° C. for 23 hours. After cooling to room temperature, the reaction mixture was diluted with ethyl acetate, and washed successively with 1N hydrochloric acid, water, brine and then dried over anhydrous sodium sulfate. Evaporation to dryness under reduced pressure gave crude methyl 2-(3-cyclohexyl-1,1,1-trifluoro-3-nitropropan-2-ylamino)-3,3-dimethylbutanoate as a mixture of isomers. Separation by silica gel chromatography, eluting with 8% ethyl acetate/hexane, gave two fractions, a faster eluting compound, 5A-1 (0.553 gm) and a slower eluting compound, 5B-1 (0.3 gm). The two compounds are different diastereoisomers of methyl 2-(3-cyclohexyl-1,1,1-trifluoro-3-nitropropan-2-ylamino)-3,3-dimethylbutanoate (5), although the absolute stereochemistry has not yet been established.

Example 4

Preparation of a Compound of Formula (6) in which R² is Cyclohexyl and R³ is Trifluoromethyl Preparation of methyl 2-(3-cyclohexyl-1,1,1-trifluoro-3-aminopropan-2-ylamino)-3,3-dimethylbutanoate

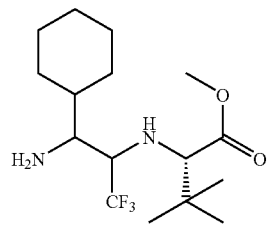

(6)

Methyl 2-(3-cyclohexyl-1,1,1-trifluoro-3-nitropropan-2-ylamino)-3,3-dimethylbutanoate (5A-1) (0.553 gm) in ethanol (70 mL) was hydrogenated over Raney Nickel catalyst at 50 psi for 16 hours. The catalyst was filtered off and the filtrate was evaporated to dryness under reduced pressure, to give crude methyl 2-(3-amino-3-cyclohexyl-1,1,1-trifluoropropan-2-ylamino)-3,3-dimethylbutanoate (6). Separation by silica gel chromatography, eluting with 10% ethyl acetate/hexane, gave two pure isomers, a faster eluting compound, 6A1-isomer A (389 mgm) and a slower eluting compound, 6A1-isomer B (57 mgm). The two compounds are different stereoisomers of methyl 2-(3-cyclohexyl-1,1,1-trifluoro-3-aminopropan-2-ylamino)-3,3-dimethylbutanoate, although the absolute stereochemistry has not yet been established.

Similarly, starting with the (5B) isomer of methyl 2-(3-cyclohexyl-1,1,1-trifluoro-3-nitropropan-2-ylamino)-3,3-dimethylbutanoate, and following the procedures of Example 4, two further stereoisomers of methyl 2-(3-cyclohexyl-1,1,1-trifluoro-3-aminopropan-2-ylamino)-3,3-dimethylbutanoate, a faster eluting compound designated as 6B1-isomer A and a slower eluting compound designated as 6B1-isomer B.

Example 5

Preparation of a Compound of Formula (7) in which $R^2$ is Cyclohexyl and $R^3$ is Trifluoromethyl Preparation of methyl 2-(3-cyclohexyl-1,1,1-trifluoro-3-(pyrazine-2-carboxamido)propan-2-ylamino)-3,3-dimethylbutanoate

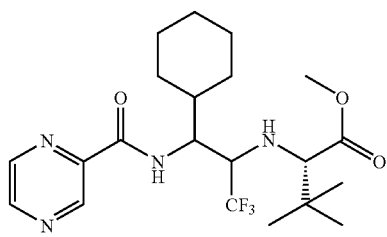

(7)

A mixture of the 6A1-isomer A of methyl 2-(3-cyclohexyl-1,1,1-trifluoro-3-aminopropan-2-ylamino)-3,3-dimethylbutanoate (389 mgm), pyrazinecarboxylic acid (65 mg), 1-ethyl-3-(3'-dimethylaminopropyl)-carbodimide ((331 mg), 1-hydroxy-benzotriazole (233 mg), and N-methylmorpholine (0.19 mL) in dichloromethane was stirred at room temperature for 24 hours. The reaction mixture was then diluted with ethyl acetate and washed successively with 1N hydrochloric acid, water, brine and then dried over anhydrous sodium sulfate. Evaporation to dryness under reduced pressure gave crude methyl 2-(3-cyclohexyl-1,1,1-trifluoro-3-(pyrazine-2-carboxamido)propan-2-ylamino)-3,3-dimethylbutanoate, an isomer of a compound of formula (7) designated as 7A1-isomer A.

In similar fashion, following the procedures of Example 5 above, reaction of the 6A1-isomer B compound (57 mg) gave a stereoisomer of a compound of formula (7) designated as 7A1-isomer B.

In similar fashion, following the procedures of Example 5 above, reaction of the 6B1-isomer A compound gave a stereoisomer of a compound of formula (7) designated as 7B1-isomer A.

In similar fashion, following the procedures of Example 5 above, reaction of the 6B1-isomer B compound gave a stereoisomer of a compound of formula (7) designated as 7B1-isomer B.

7A1-isomer A, 7A1-isomer B, 7B1-isomer A, and 7B1-isomer B are different stereoisomers of methyl 2-(3-cyclohexyl-1,1,1-trifluoro-3-aminopropan-2-ylamino)-3,3-dimethylbutanoate, although the absolute stereochemistry of each has not yet been established.

Example 6

Alternative Preparation of a Compound of Formula (7) in which $R^2$ is Cyclohexyl and $R^3$ is Trifluoromethyl Preparation of methyl 2-(3-cyclohexyl-1,1,1-trifluoro-3-(pyrazine-2-carboxamido)propan-2-ylamino)-3,3-dimethylbutanoate

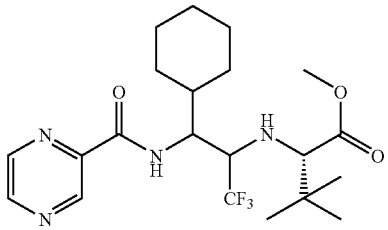

(7)

Methyl 2-(3-cyclohexyl-1,1,1-trifluoro-3-nitropropan-2-ylamino)-3,3-dimethylbutanoate (isomer 5B1, 0.3 gm) in ethanol (30 mL) was hydrogenated over Raney Ni catalyst at 50 psi for 20 hours. The catalyst was filtered off and the filtrate was evaporated to dryness under reduced pressure, to provide crude methyl 2-(3-amino-3-cyclohexyl-1,1,1-trifluoropropan-2-ylamino)-3,3-dimethylbutanoate (6) which was used in the next reaction with no further purification.

The crude material was dissolved in methylene dichloride (4 mL) and tetrahydrofuran (0.5 mL) and treated with pyrazinecarboxylic acid (0.146 gm, 1.5 eq), hydroxybenztriazole (0.159 gm, 1.5 eq), and N-methylmorpholine (0.13 mL, 1.5 eq). After stirring at room temperature for 72 hours the reaction mixture was diluted with ethyl acetate and washed successively with 1N hydrochloric acid, water, brine and then dried over anhydrous sodium sulfate. Evaporation to dryness under reduced pressure gave crude methyl 2-(3-cyclohexyl-1,1,1-trifluoro-3-(pyrazine-2-carboxamido)propan-2-ylamino)-3,3-dimethylbutanoate. Separation by silica gel chromatography, eluting with 15% ethyl acetate/hexane, gave two pure isomers, a faster eluting band, designated as isomer 7B1-isomer A, and a slower eluting band, designated as 7B1-isomer B.

Similarly, starting with the stereoisomer of formula (5A1), the stereoisomers designated as 7A1-isomer A and 7A1-isomer B are obtained.

Example 7

Preparation of a Compound of Formula (8) in which $R^2$ is Cyclohexyl and $R^3$ is Trifluoromethyl Preparation of 2-(3-cyclohexyl-1,1'-trifluoro-3-(pyrazine-2-carboxamido)propan-2-ylamino)-3,3-dimethylbutanoic acid

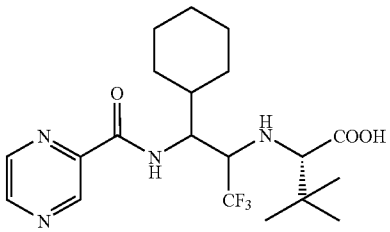

(8)

The stereoisomer of methyl 2-(3-cyclohexyl-1,1,1-trifluoro-3-(pyrazine-2-carboxamido)propan-2-ylamino)-3,3-dimethylbutanoate designated as 7A1-isomer A (107 mgm), and potassium trimethylsilanolate (124 mgm, 4 eq) in tetrahydrofuran (2.5 mL) were heated to 140° C. in a microwave apparatus for 10 minutes. The reaction mixture was diluted with ethyl acetate, and washed successively with 1N hydrochloric acid, water, brine, and then dried over anhydrous sodium sulfate. Evaporation to dryness under reduced pressure gave crude 2-(3-cyclohexyl-1,1,1-trifluoro-3-(pyrazine-2-carboxamido)propan-2-ylamino)-3,3-dimethylbutanoic acid (8), designated as 8A1-isomer A.

Similarly, starting with the stereoisomer designated as 7A1 isomer B (89 mg), and following the procedure of Example 7, a stereoisomer designated as 8A1 isomer B was obtained.

Similarly, starting with the stereoisomer designated as 7B1 isomer A (83 mg), and following the procedure of Example 7, a stereoisomer designated as 8B1 isomer A was obtained.

Similarly, starting with the stereoisomer designated as 7B1 isomer B (68 mg), and following the procedure of Example 7, a stereoisomer designated as 8B1 isomer B was obtained.

Example 8

Preparation of a Compound of Formula (10) in which $R^2$ is Cyclohexyl and $R^3$ is Trifluoromethyl Preparation of (1S,3aR,6aS)-ethyl 2-(2-(3-cyclohexyl-1,1,1-trifluoro-3-(pyrazine-2-carboxamido)propan-2-ylamino)-3,3-dimethylbutanoyl)octahydrocyclopenta[c]pyrrole-1-carboxylate

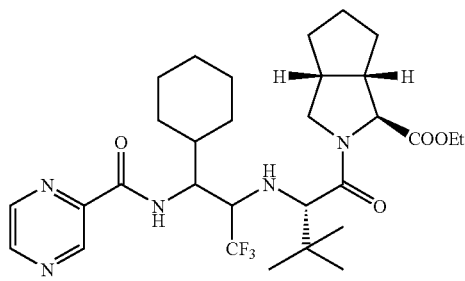

(10)

The stereoisomer of 2-(3-cyclohexyl-1,1,1-trifluoro-3-(pyrazine-2-carboxamido)propan-2-ylamino)-3,3-dimethylbutanoic acid designated as 8A1-isomerA (crude product from above), (1S,3aR,6aS)-ethyl octahydrocyclopenta[c]pyrrole-1-carboxylate (9) (1 eq), N-methylmorpholine (0.106 mL, 2.5 eq) and O-(7-azabenzotriazole-1-yl)-N,N,N,N'-tetramethyluronium hexafluorophosphate (101 mgm, 1 eq) in a mixture of N,N-dimethylformamide (1.2 mL) and tetrahydrofuran (0.2 mL) was stirred at room temperature for 18 hours. The reaction mixture was then diluted with ethyl acetate and washed successively with 1N hydrochloric acid, water, brine and then dried over anhydrous sodium sulfate. Evaporation to dryness under reduced pressure gave crude product, which was purified by silica gel column chromatography. Elution with a solvent gradient from hexane to 20% ethyl acetate/hexane gave pure (1S,3aR,6aS)-ethyl 2-(2-(3-cyclohexyl-1,1,1-trifluoro-3-(pyrazine-2-carboxamido)propan-2-ylamino)-3,3-dimethylbutanoyl)octahydrocyclopenta-[c]pyrrole-1-carboxylate, designated as 10A1-isomer A.

Similarly, starting with the stereoisomer designated as 8A1 isomer B, and following the procedure of Example 8, a stereoisomer designated as 10A1 isomer B (14 mg) was obtained.

Similarly, starting with the stereoisomer designated as 8B1 isomer A, and following the procedure of Example 8, a stereoisomer designated as 10B1 isomer A (16 mg) was obtained.

Similarly, starting with the stereoisomer designated as 8B1 isomer B (68 mg), and following the procedure of Example 8, a stereoisomer designated as 10B1 isomer B was obtained.

Example 9

Preparation of a Compound of Formula I in which $R^2$ is Cyclohexyl and $R^3$ is Trifluoromethyl Preparation of (1S,3aR,6aS)-2-((2S)-2-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide

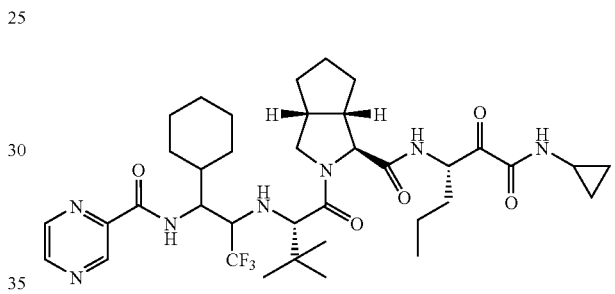

The stereoisomer of (1S,3aR,6aS)-ethyl 2-(2-(3-cyclohexyl-1,1,1-trifluoro-3-(pyrazine-2-carboxamido)propan-2-ylamino)-3,3-dimethylbutanoyl)octahydrocyclopenta[c]pyrrole-1-carboxylate, designated as 10A1-isomer-A (85 mg) was dissolved in ethanol (3 mL) and treated with 2N aqueous sodium hydroxide solution (0.665 mL) at 65° C. for 2 hours. The reaction mixture was then diluted with ethyl acetate and washed successively with 1N hydrochloric acid, water, brine and then dried over anhydrous sodium sulfate. Evaporation to dryness under reduced pressure gave the crude acid, designated as 11A1-isomer A, an isomer of (1S,3aR,6aS)-2-(2-(3-cyclohexyl-1,1,1-trifluoro-3-(pyrazine-2-carboxamido)propan-2-ylamino)-3,3-dimethylbutanoyl)octahydrocyclopenta[c]pyrrole-1-carboxylic acid. The crude compound of formula 11A1-isomer A was mixed with N-methylmorpholine (0.078 mL, 5 eq), 1-hydroxybenzotriazole (38.6 mgm, 2 eq), 1-ethyl-3-(3'-dimethylaminopropyl)carbodimide (55 mgm, 2 eq), and (3S)-3-amino-N-cyclopropyl-2-hydroxyhexanamide hydrochloride (12) (123 mgm, 4 eq) and dissolved in a mixture of tetrahydrofuran and dichloromethane, and stirred at room temperature for 18 hours. The reaction mixture was then diluted with ethyl acetate, washed successively with 1N hydrochloric acid, water, brine and then dried over anhydrous sodium sulfate. Evaporation to dryness under reduced pressure gave crude product (13A1-isomer A), an isomer of (1S,3aR,6aS)-2-(2-(3-cyclohexyl-1,1,1-trifluoro-3-(pyrazine-2-carboxamido)propan-2-ylamino)-3,3-dimethylbutanoyl)-N-((3S)-1-(cyclopropylamino)-2-hydroxy-1-oxohexan-3-yl)octahydrocyclopenta[c]pyrrole-1-carboxamide.

The product of formula 13A1-isomer A was then dissolved in dichloromethane and treated with the Dess Martin periodinanane reagent (76 mg, 2 eq) for 1 hour at room temperature. The reaction mixture was then diluted with ethyl acetate, washed successively with dilute sodium bicarbonate solution, water, brine and then dried over anhydrous sodium sulfate. Evaporation to dryness under reduced pressure provided a crude product which was purified by silica gel column chromatography, eluting with a solvent gradient from hexane to 50% ethyl acetate/hexane, to provide a pure stereoisomer of (1S,3aR,6aS)-2-((2S)-2-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide, designated as Formula I isomer A. Mass Spectrum: M+ 734.2. NMR: 500 MHz CDCl$_3$ Y: 0.6 (m, 2H), 0.9 (m), 0.95 (s, 9H), 1.1-2.00 (m), 2.77 (m, 1H), 2.82 (m), 3.00-3.10 (m, 2H), 3.40 (s, 1H), 3.44 (dd, 1H), 3.63 (dd, 1H), 4.30 (m, 1H), 4.48 (s, 1H), 5.25 (m, 1H), 6.95 (m, 1H), 7.20 (d, 1H), 8.20 (d, 1H), 8.55 (m, 1H), 8.78 (s, 1H), 9.40 (s, 1H).

Similarly, starting with the stereoisomer designated as 10A1-isomer B, and following the procedures of Example 9, a pure stereoisomer of (1S,3aR,6aS)-2-((2S)-2-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide, designated as Formula I isomer B, was obtained. Mass Spectrum: M+ 734.4; NMR: 500 MHz CDCl$_3$ γ: 0.6 (m, 2H), 0.8-2.00 (m), 2.80 (m, 2H), 2.95-3.10 (m, 2H), 3.37 (s, 1H), 3.42 (dd, 1H), 3.60 (dd, 1H), 4.30 (m, 1H), 4.58 (s, 1H), 5.25 (m, 1H), 6.95 (m, 1H), 7.30 (d, 1H), 7.93 (d, 1H), 8.60 (m, 1H), 8.80 (s, 1H), 9.40 (s, 1H).

Similarly, starting with the stereoisomer designated as 10B1-isomer A, and following the procedures of Example 9, a pure stereoisomer of (1S,3aR,6aS)-2-((2S)-2-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide, designated as Formula I isomer C, was obtained. Mass Spectrum: M+ 734.7; NMR: 500 MHz CDCl$_3$ Y: 0.55 (m, 2H), 0.7-2.0 (m, 36H), 2.4 (m, 1H), 2.80 (m, 3H), 3.10 (s, 3H), 3.23 (m, 1H), 3.40 (m, 1H), 3.60 (m, 1H), 4.25 (m, 1H), 4.43 (s, 1H), 5.22 (m, 1H), 6.85 (m, 1H), 7.10 (d, 1H), 8.1 (d, 1H), 8.45 (s, 1H), 8.70 (s, 1H), 9.37 (s, 1H).

Similarly, starting with the stereoisomer designated as 10B 1-isomer B, and following the procedures of Example 9, a pure stereoisomer of (1S,3aR,6aS)-2-((2S)-2-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide, designated as Formula I isomer D, was obtained. Mass Spectrum: M+ 734.5; NMR: 500 MHz CDCl$_3$ γ: 0.6 (m, 2H), 0.85 (m), 1.00 (s, 9H), 1.1-1.95 (m, 23H), 2.75 (m, 1H), 2.85 (m, 2H), 3.15 (s, 1H), 3.23 (m, 1H), 3.35 (m, 1H), 3.63 (m, 1H), 4.25 (t, 1H), 4.43 (s, 1H), 5.25 (m, 1H), 6.87 (m, 1H), 7.03 (d, 1H), 7.97 (d, 1H), 8.55 (s, 1H), 8.78 (s, 1H), 9.40 (s, 1H).

The stereoisomers designated as Formula I isomer A, Formula I isomer B, Formula I isomer C, and Formula I isomer D, prepared as described in the above examples, are the compounds of the invention shown as Formula IA, IB, IC, and ID, which are named as:

IA: (1S,3aR,6aS)-2-((S)-2-((2S,3R)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

IB: (1S,3aR,6aS)-2-((S)-2-((2R,3S)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

IC: (1S,3aR,6aS)-2-((S)-2-((2S,3S)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

ID: (1S,3aR,6aS)-2-((S)-2-((2R,3R)-(3-cyclohexyl-1,1,1-trifluoro-3-(pyrazine-2-carboxamido)propan-2-ylamino)-3,3-dimethylbutanoyl)-N-((S)-1-(cyclopropylamino)-1,2-dioxohexan-3-yl)octahydrocyclopenta[c]pyrrole-1-carboxamide.

However, as explained above, the absolute stereochemistry of the compounds has not yet been established, and it should be understood that although all four stereoisomers have been isolated and tested, Formula I isomer A does not necessarily correspond to Formula IA, Formula I isomer B does not necessarily correspond to Formula IB, etc.

Example 10

Preparation of a Compound of Formula (16)

Preparation of (1 S,3aR,6aS)-2-((S)-2-(tert-butoxycarbonylamino)-3,3-dimethylbutanoyl)octahydrocyclopenta[c]pyrrole-1-carboxylic acid

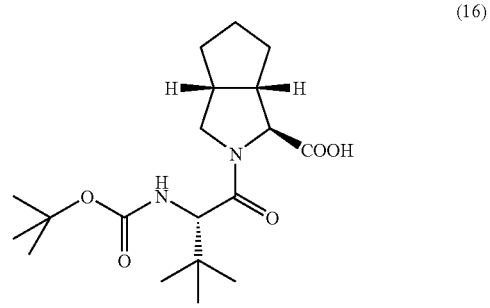

(16)

(1S,3aR,6aS)-ethyl octahydrocyclopenta[c]pyrrole-1-carboxylate, the compound of formula (9) as the free base (34 mg), L-N-Boc-tert-butylglycine, the compound of formula (14) (43 mg, 1.0 eq), 1-hydroxybenzotriazole (HOBT) (25.2 mg, 1.0 eq), and N,N'-dicyclohexylcarbodiimide (~0.2 mL, 1.0 eq) was dissolved in dichloromethane (3 mL) and tetrahydrofuran (2 mL) at room temperature. After 18 hours at room temperature the solution was diluted with more dichloromethane, filtered through a glass flit, and the filtrate evaporated to dryness. The crude product was dissolved in methanol (5 mL) and treated with 1N aqueous sodium hydroxide solution (4 mL) at room temperature. After 30 minutes the reaction mixture was diluted with water and washed with a small amount of diethyl ether. The aqueous layer was acidified with 1N aqueous hydrochloric acid and the product extracted into ethyl acetate. The organic extract was washed with brine, dried and evaporated to dryness under reduced pressure to give crude (1S,3aR,6aS)-2-((S)-2-(tert-butoxycarbonylamino)-3,3-dimethylbutanoyl)octahydrocyclopenta

[c]pyrrole-1-carboxylic acid (15), which was used in the next reaction without further purification.

Example 11

Preparation of a Compound of Formula (17)

Preparation of tert-butyl (2S)-1-((1S,3aR,6aS)-1-((3S)-1-(cyclopropylamino)-2-hydroxy-1-oxohexan-3-ylcarbamoyl)hexahydrocyclopenta-[c]pyrrol-2(1H)-yl)-3,3-dimethyl-1-oxobutan-2-ylcarbamate

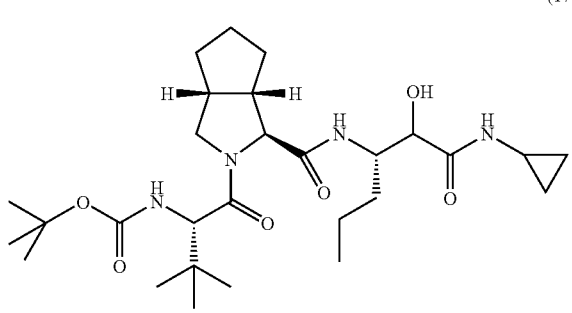

(17)

The crude (1S,3aR,6aS)-2-((S)-2-(tert-butoxycarbonylamino)-3,3-dimethylbutanoyl)octahydrocyclopenta[c]pyrrole-1-carboxylic acid from Example 10 was dissolved in dichloromethane (4 mL) and treated with 1-ethyl-3-(3'-dimethylaminopropyl)carbodiimide (EDCI) (71 mg, 2 eq), 1-hydroxybenzotriazole (HOBT) (57 mg, 2 eq) and N-methyl morpholine (0.2 mL, 5 eq) at room temperature. To this mixture was added after 30 minutes (3S)-3-amino-N-cyclopropyl-2-hydroxyhexanamide, the compound of formula (12) (1 eq) in dichloromethane (3 mL) and N,N-dimethylformamide (3 mL) and the reaction mixture was stirred at room temperature. After 18 hours the reaction mixture was diluted with water, and the product extracted into ethyl acetate. The organic extract was washed with brine, dried and evaporated to dryness under reduced pressure, to give crude tert-butyl (2S)-1-((1S,3aR,6aS)-1-((3S)-1-(cyclopropylamino)-2-hydroxy-1-oxohexan-3-ylcarbamoyl)hexahydrocyclopenta-[c] pyrrol-2(1H)-yl)-3,3-dimethyl-1-oxobutan-2-ylcarbamate, the compound of formula (17).

Example 12

Preparation of a Compound of Formula (18)

Preparation of 2,2,2-trifluoro-1-(pyrazin-2-yl)ethanone

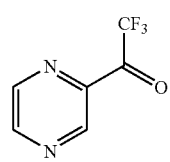

(18)

Pyrazine carboxylate methyl ester (7 g) was dissolved in dimethoxy ethane (monoglyme) (20 mL) and treated at room temperature with trimethylsilyltrifluoro-methane (10 mL; 1.44 eq) and caesium fluoride (0.77 g; 0.1 eq) that had been freshly dried at for 10 minutes under vacuum while being heated with a heat gun. After 18 hours at room temperature the reaction mixture was concentrated under reduced pressure at room temperature, and the residue was dissolved in tetrahydrofuran (50 mL) and acetic acid (20 mL) and treated with tert-butylammonium fluoride (50 mL; 1M THF solution) for 3 hours at room temperature. The reaction was diluted with ethyl acetate, and washed with dilute aqueous sodium bicarbonate solution (3 times), brine, dried over anhydrous sodium sulfate, and evaporated to dryness under reduced pressure to an oil. Trituration of the oil with dichloromethane/hexane gave 2,2,2-trifluoro-1-(pyrazin-2-yl)ethanone (18) as a brown solid (2.9 g).

Example 13

Preparation of a Compound of Formula (20) in which $R^2$ is Cyclohexyl

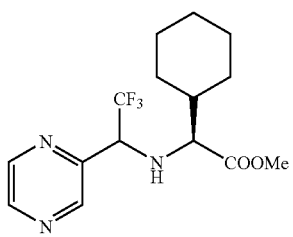

(20)

A mixture of 2,2,2-trifluoro-1-(pyrazin-2-yl)ethanone (18) (1.27 g, 1 eq), L-cyclohexaneglycine methyl ester hydrochloride (1.5 g, 1 eq) and diisopropylethylamine (5 mL, 4 eq) were dissolved in dry N,N-dimethylformamide (30 mL) and dry tetrahydrofuran (10 mL), and titanium tetrachloride (6.49 mL, 1M in dichloromethane) was added slowly to the stirred solution under a nitrogen atmosphere at room temperature. After 15 hours a further portion of titanium tetrachloride (4.3 mL, 1M in dichloromethane) was added, and the reaction mixture stirred for a further 3 hours at room temperature. A solution of sodium cyanoborohydride ($NaCNBH_4$, 1.5 gm, 3.2 eq) in methanol (11 mL) was slowly added to the stirred reaction mixture. After 2.5 hours at room temperature the reaction mixture was dilute with ethyl acetate (150 mL), and filtered through a pad of anhydrous magnesium sulfate. Evaporation of the filtrate under reduced pressure gave a yellow oily solid, which was chromatographed on silica gel. Eluting with ethyl acetate/pentane (3:10) gave a faster eluting band, designated as 20-Isomer A1 (451 mg), and a slower eluting band, designated as 20-Isomer B1 (445 mg).

One of 20-Isomer A1 and 20-Isomer B1 is (2S)-methyl 2-cyclohexyl-2-((2R)-2,2,2-trifluoro-1-(pyrazin-2-yl)ethylamino)acetate, and the other (2S)-methyl 2-cyclohexyl-2-((2S)-2,2,2-trifluoro-1-(pyrazin-2-yl)ethylamino)acetate, although at this time the absolute assignment of stereochemistry for the two stereoisomers has not been determined.

Example 14

Preparation of a Compound of Formula (21) in which R² is Cyclohexyl

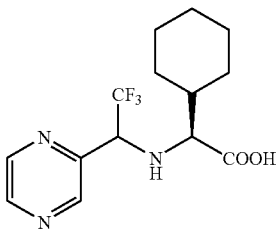

(21)

A solution of 20-Isomer A1 (170 mg, from Example 13 above), was dissolved in carbon tetrachloride (5 mL) and cooled to 0° C. under a nitrogen atmosphere. Trimethylsilyliodide (0.7 mL, 10 eq) was added, and the reaction mixture heated to 50° C. for 47 hours. It was then diluted with dichloromethane, and washed with 10% aqueous sodium thiosulfate ($Na_2S_2O_3$) solution (3 times), brine, dried over anhydrous magnesium sulfate, and evaporated to dryness under reduced pressure to give a compound designated as 21 Isomer A1 (93 mgm), which is either (2S)-2-cyclohexyl-2-((2R)-2,2,2-trifluoro-1-(pyrazin-2-yl)ethylamino)acetic acid, or (2S)-2-cyclohexyl-2-((2S)-2,2,2-trifluoro-1-(pyrazin-2-yl)ethylamino)acetic acid, depending upon the stereochemistry of the starting material, which has not been established at this time.

Similarly, starting with 20-Isomer B1 (200 mg, from Example 13 above), a compound designated as 21-Isomer B1 was obtained, which is either (2S)-2-cyclohexyl-2-((2R)-2,2,2-trifluoro-1-(pyrazin-2-yl)ethylamino)acetic acid, or (2S)-2-cyclohexyl-2-((2S)-2,2,2-trifluoro-1-(pyrazin-2-yl)ethylamino)acetic acid, depending upon the stereochemistry of the starting material, which has not been established at this time.

Example 15

Preparation of a Compound of Formula (22)

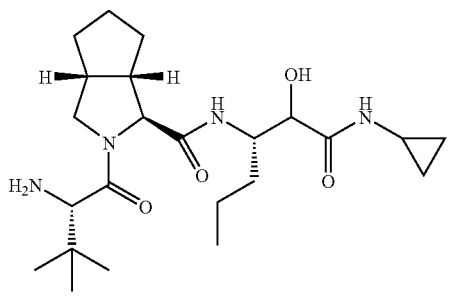

(22)

The compound designated as (17) in Example 11 in dichloromethane (3 mL) was treated with trifluoroacetic acid (3 mL) for 1 hour at room temperature. Toluene was then added, and the solution evaporated to dryness under reduced pressure, to provide (1S,3aR,6aS)-2-((S)-2-amino-3,3-dimethylbutanoyl)-N-((3S)-1-(cyclopropylamino)-2-hydroxy-1-oxohexan-3-yl)octahydrocyclopenta[c]pyrrole-1-carboxamide, the compound of formula (22), which was used in the next reaction with no further purification.

Example 16

Preparation of a Compound of Formula (23) in which R² is Cyclohexyl

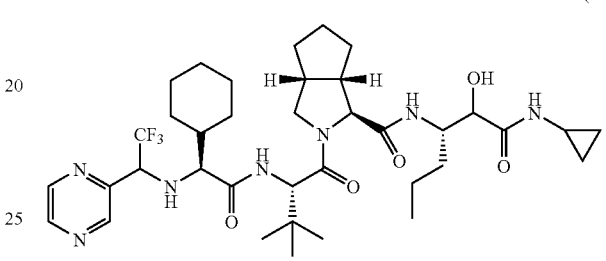

(23)

The compound of formula (22), prepared as described in Example 15, was dissolved in dichloromethane (3 mL) and N,N-dimethylformamide (3 mL), and treated with a solution of the compound designated as 21-Isomer A1 (I 7 mg), 1-ethyl-3-(3'-dimethylaminopropyl)carbodiimide (EDCI) (20 mg), 1-hydroxybenzotriazole (HOBT) (20 mg), N-methylmorpholine (0.05 mL) in dichloromethane (3 mL). After 18 hours at room temperature the reaction mixture was diluted with ethyl acetate, washed with 1N aqueous hydrochloric acid, dilute aqueous sodium bicarbonate solution, brine, then dried over anhydrous sodium sulfate, and evaporated under reduced pressure to give a compound designated as 23-Isomer A1, which is either (1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide or (1S,3aR,6aS)-2-((S)-2-((R)-2-cyclohexyl-2-((S)-2,2,2-trifluoro-1-(pyrazin-2-yl)ethylamino)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide, although the absolute stereochemistry has not yet been established.

Similarly, replacing the compound designated as 21-Isomer A1 with the compound designates as 21-Isomer B1, and following the procedure of Example 16, the other stereoisomer of a compound of formula (23) is obtained, designated as 23-Isomer B1, which is either (1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide or (1S,3aR,6aS)-2-((S)-2-((R)-2-cyclohexyl-2-((S)-2,2,2-trifluoro-1-(pyrazin-2-yl)ethylamino)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide.

Example 17

Preparation of a Compound of Formula I in which $R^1$ is Trifluoromethyl and $R^2$ is Cyclohexyl

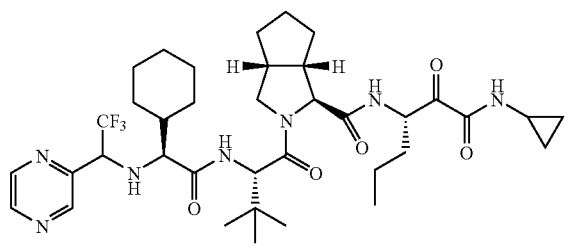

Formula I

The compound designated as 23-Isomer A1 was dissolved in dichloromethane (10 mL), and treated with Dess-Martin periodinane (48 mg) for 3.5 hours at room temperature. The reaction mixture was then diluted with ethyl acetate, and washed with 0.26M sodium thiosulfate ($Na_2S_2O_3$) solution, dilute aqueous sodium bicarbonate solution, brine, and then dried over anhydrous sodium sulfate. Removal of the solvent under reduced pressure gave a crude compound, purification of which by reverse phase preparative HPLC gave 20 mg of a pure compound that was designated as Formula I isomer E. Mass Spectrum: Calc MWt 733.875. Found $(M+1)^+$ 734.6. This compound is either (1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N-((S)-1-(cyclopropylamino)-1,2-dioxohexan-3-yl)octahydrocyclopenta[c]pyrrole-1-carboxamide (IE), or (1S,3aR,6aS)-2-((S)-2-((S)-2-cyclohexyl-2-((R)-2,2,2-trifluoro-1-(pyrazin-2-yl)ethylamino)acetamido)-3,3-dimethylbutanoyl)-N-((S)-1-(cyclopropylamino)-1,2-dioxohexan-3-yl)octahydrocyclopenta[c]pyrrole-1-carboxamide (IF). However, the absolute stereochemistry of these stereoisomers has not yet been established at this time.

Similarly, starting with the compound designated as 23-Isomer B1, and following the procedure of Example 16, the other stereoisomer was obtained, designated as Formula I isomer F. Mass Spectrum: Calc MWt 733.875. Found (M+1)+734.6. This compound is either (1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N-((S)-1-(cyclopropylamino)-1,2-dioxohexan-3-yl)octahydrocyclopenta[c]pyrrole-1-carboxamide (IE), or (1S, 3aR,6aS)-2-((S)-2-((S)-2-cyclohexyl-2-((R)-2,2,2-trifluoro-1-(pyrazin-2-yl)ethylamino)acetamido)-3,3-dimethylbutanoyl)-N-((S)-1-(cyclopropylamino)-1,2-dioxohexan-3-yl)octahydrocyclopenta[c]pyrrole-1-carboxamide (IF).

Example 18

Hard gelatin capsules containing the following ingredients are prepared:

| Ingredient | Quantity (mg/capsule) |
|---|---|
| Compound of Formula I | 30.0 |
| Starch | 305.0 |
| Magnesium stearate | 5.0 |

The above ingredients are mixed and filled into hard gelatin capsules.

Example 19

A dry blend formulation is prepared containing the following components:

| Ingredient | Quantity (mg/tablet) |
|---|---|
| Compound of Formula I | 25.0 |
| Cellulose, microcrystalline | 200.0 |
| Colloidal silica | 10.0 |
| Stearic acid | 5.0 |

The components are blended and compressed to form tablets.

Example 20

A dry powder inhaler formulation is prepared containing the following components:

| Ingredient | Weight % |
|---|---|
| Compound of Formula I | 5 |
| Lactose | 95 |

The compound of Formula I is mixed with the lactose and the mixture is added to a dry powder inhaling appliance.

Example 21

Tablets, each containing 30 mg of active ingredient, the compound of Formula I, are prepared as follows:

| Ingredient | Quantity (mg/tablet) |
|---|---|
| Compound of Formula I | 30.0 |
| Starch | 45.0 |
| Microcrystalline cellulose | 35.0 |
| Polyvinylpyrrolidone | 4.0 |
| As a 10% solution in sterile water | |
| Sodium carboxymethyl starch | 4.5 |
| Magnesium stearate | 0.5 |
| Talc | 1.0 |
| TOTAL | 120 |

The compound of Formula I, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 22

Suppositories, each containing 25 mg of active ingredient are made as follows:

| Ingredient | Amount |
| --- | --- |
| Compound of Formula I | 25 mg |
| Saturated fatty acid glycerides | To 2000 mg |

The compound of Formula I is passed through a No. 60 mesh U.S. sieve and suspended in the saturated fatty acid glycerides that were previously melted using the minimum heat necessary. The mixture is then poured into a suppository mold of nominal 2.0 g capacity and allowed to cool.

Example 23

Suspensions, each containing 50 mg of active ingredient per 5.0 mL dose, are made as follows:

| Ingredient | Amount |
| --- | --- |
| Compound of Formula I | 50.0 mg |
| Xanthan gum | 4.0 mg |
| Sodium carboxymethyl cellulose | 11% |
| Microcrystalline cellulose (89%) | 50 mg |
| Sucrose | 1.75 g |
| Sodium benzoate | 10 mg |
| Flavor and color | q.v |
| Purified water | 5.0 ml |

The compound of Formula I, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume. Optionally, a surfactant such as Tween 80 can be added.

Example 24

A subcutaneous formulation may be prepared as follows:

| Ingredient | Quantity |
| --- | --- |
| Compound of Formula I | 5.0 mg |
| Corn oil | 1.0 ml |

Example 25

An injectable preparation is prepared having the following composition:

| Ingredients | Amounts |
| --- | --- |
| Compound of Formula I | 2.0 mg/ml |
| Mannitol, USP | 50 mg/ml |
| Gluconic acid, USP | q.s. (pH 5-6) |
| Water (distilled, sterile) | q.s. to 1.0 ml |

The injectable preparation is then sterilized, or sterile filtration is carried out.

Example 26

A topical preparation is prepared having the following composition:

| Ingredients | Amounts |
| --- | --- |
| Compound of Formula I | 0.2-10 g |
| Span 60 | 2.0 |
| Tween 60 | 2.0 |
| Mineral oil | 5.0 |
| Petrolatum | 0.1 |
| Methyl paraben | 0.15 |
| Propyl paraben | 0.05 |

All of the above ingredients, except water, are combined and heated to 60° C. with stirring. A sufficient quantity of water at 60° C. is then added with vigorous stirring to emulsify the ingredients, and water then added q.s. 100 g.

Example 27

Sustained Release Composition

| Ingredients | Weight Range (%) |
| --- | --- |
| Compound of Formula I | 50-95 |
| Microcrystalline cellulose | 1-35 |
| Methacrylic acid copolymer | 1-35 |
| Sodium hydroxide | 0.1-1.0 |
| Hydroxypropylmethylcellulose | 0.5-5.0 |
| Magnesium stearate | 0.5-5.0 |

The sustained release formulations of this invention are prepared as follows: the compound of Formula I and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Rohm. Phamma), and the like. These film-forming agents may optionally contain colorants, plasticizers, and other supplemental ingredients.

Example 28

Protocol for Cathepsin S Enzyme Activity Assay

The test compounds, dissolved in DMSO, are tested for their ability to inhibit the enzymatic activity of recombinant human cathepsin S. $IC_{50}$ (concentration at which 50% of enzymatic activity is inhibited relative to maximal activity) are calculated by interpolation. The cysteine protease inhibitor E-64 is assayed in parallel as a positive control.

Human recombinant cathepsin S is incubated with compounds or vehicle (final concentration=1% DMSO vehicle) in the presence of peptide substrate which is 10 uM Z-Leu-Arg-AMC. Compounds are preincubated with the enzyme for 15 minutes at 25° C. and the reaction started by the addition of substrate. Incubation with substrate proceeds for 30 minutes at 25° C. Incubation buffer is 20 mM $CH_3COONa$, pH 4.5, 2.5 mM DTT, 0.05 M NaCl. Cathepsin S-mediated substrate cleavage is quantified using spectofluorimetric quantitation of AMC.

Results

| Compound | Cathepsin S $IC_{50}$ |
|---|---|
| Formula I isomer A | 4.1 nM |
| Formula I isomer B | 0.6 nM |
| Formula I isomer C | 2.0 nM |
| Formula I isomer D | 0.6 nM |
| Formula I isomer E | 1.8 nM |
| Formula I isomer F | 1.4 nM |

Example 29

Cellular Activity Assay for Cathepsin S Inhibitors

The processing of invariant chain (Ii) is regulated by Cathepsin S. Proper processing of Invariant chain by cathepsin S is required for the chaperone function of invariant chain, which is to regulate the intracellular maturation, folding, and antigen binding of Class II MHC molecules. A 10 kDa intermediate in the processing of invariant chain, referred to as Iip10, is the substrate for cathepsin S. Inhibition of cathepsin S results in a block in the maturation of the Iip10 intermediate in cells, and inhibition of both invariant chain processing and Class II MHC maturation. Compounds, dissolved in DMSO, are incubated with the human Raji B cell line for 4 hours in the presence of serum. Lysates are then produced from these cells and the invariant chain protein intermediates separated by SDS-PAGE and analyzed by western blot. The accumulation of the Iip10 intermediate induced by cathepsin S inhibition is visualized by western blotting with antibodies specific for human invariant chain. The level of invariant chain can be quantified using densitometry.

This assay was used to confirm the affect of the compounds of the invention on cellular cathepsin S, and to confirm their use as agents for the treatment of autoimmune disease.

Protocol

Cathepsin S Cellular Assay

In Vitro Iip10 Accumulation Assay in Raji Cells

Raji cells were maintained in appropriate cell culture conditions, as suspension cells, splitting every 3-4 days. The cells were split 1-2 days prior to assay.

Raji cells were plated in wells of 24-well plates at a density of $10^6$ cells in 0.5 ml of RPMI medium 1640 containing 10% (v/v) FBS (heat inactivated), 10 mM HEPES, 2 mM L-glutamine, 1 mM sodium pyruvate, and 1% penicillin-streptomycin. The final cell density was $2 \times 10^6$ cells/ml. This was done the morning of the assay.

Cells were treated with four concentrations (10 nM, 100 nM, 1 uM, 10 uM) of a compound of Formula I or 0.02% DMSO vehicle for four hours at 37° C. in a tissue culture incubator. An appropriate dose as 2× stock in 0.5 ml of medium was added to each well. Non-treated wells received 0.5 ml of medium+0.02% DMSO. The total volume in well=1 ml.

After the culture period (4 hours), cells are collected from wells with plastic transfer pipettes and transferred to 1.5 ml microfuge tubes and centrifuged at 2,000 rpm (setting 2 on Eppendorf microcentrifuge) for 2 minutes in a refrigerated bench top microfuge. Supernatants were removed and the pellets were gently suspended in 1 ml of cold PBS and centrifuged for 2 minutes at 2,000 rpm.

The cell pellets were then lysed in ice-cold NP-40 lysis buffer (5 mM EDTA, 1% NP-40, 150 mM NaCl, and 50 mM Tris, pH 7.6) supplemented fresh with protease inhibitors (Roche, Complete Mini, EDTA-free, Protease Inhibitor cocktail tablet, #11836170001, 1 tablet/10 ml lysis buffer). 40 µl of lysis buffer was added to each cell pellet and cooled on ice for 15 minutes.

The lysates were clarified by centrifugation for 10 minutes at 12,000 rpm at 4° C. in a bench-top microfuge. The lysates (leaving any pellet remaining in tube) were transferred to clean microfuge tubes and the lysates stored at −80° C. for future analysis.

Western Blot Analysis for Iip10

Complete analysis of lysates obtained as described above. Approximately 20 ug of protein was needed per lane for analysis on western blots for Iip10 accumulation. This was approximately 15 ul of the lysates described above.

Proteins were separated by electrophoresis on 12% Invitrogen NuPAGE Bis-Tris gels, or 12% Biorad Criterion XT gels.

15 ul of the lysates were mixed with reducing sample buffer for Bis-Tris gels from Invitrogen. Samples were heated to 100 degrees C. for 5 minutes.

Gels were run using Invitrogen NuPAGE MES running buffer. The gels were run at constant voltage.

The gels were transferred to nitrocellulose membranes in NuPAGE transfer buffer containing 20% methanol at 90V for 35 minutes in a cold room.

Blots were blocked in TBS-Tween (0.1% Tween)+5% non-fat dry milk overnight at 4 degrees C. while shaking.

Blots were incubated with primary antibody against human CD74 diluted in blocking buffer (TBS-Tween+5% milk), at room temperature, for 2 hrs while rocking. A final concentration of 2 ug/ml antibody, mouse anti-CD74 monoclonal Pin-1 antibody (Stressgen Biotechnologies #CSA-170) was used.

Blots were washed 3 times in TBS-Tween over 30 minutes.

Blots were incubated with secondary antibody, also diluted in blocking buffer, for 2 hours at room temperature while rocking. Secondary antibody (HRP-conjugated donkey anti-mouse IgG, Jackson Immunoresearch, Cat #715-035-150) was diluted 1:10,000.

Blots were washed extensively in TBS-Tween over 30 minutes.

The signal was visualized with ECL, and exposed to Kodak BioMax ML film.

If quantitation was desired, the gels were scanned and saved as TIF files, and Kodak 1D Image Analysis Software for quantitation by densitometry was carried out on the TIF files.

The compounds of Formula I were confirmed to be inhibitors of cathepsin S.

Example 30

HCV Replicon Assay

The HCV replicon assay is a cell-culture system that mimics in vivo HCV replication and provides a system to study HCV replication in vitro. It was created by transfecting cloned viral RNA derived from a consensus HCV genomic sequence into human Huh7 hepatoma cells that are semi-permissive for viral RNA production (Lohmann V., Korner F., Koch J.-O., Herian U., Theilmann L. and Bartenschlager R. (1999). Replication of subgenomic Hepatitis C virus RNAs in a hepatoma cell line. Science 285, 110-113 and Blight K. J., Kolykhalov A. A. and Rice C. M. (2000). Efficient initiation of HCV RNA Replication in cell culture. Science 290, 972-1974). These transfected cell lines contain a subgenomic HCV RNA genome that includes (1) the HCV 5'NTR fused to 12 amino acids of the capsid coding region, (2) the neomycin phosphotransferase gene (Neo) as a selectable marker, (3) the internal ribosome entry site (IRES) from encephalomyocarditis virus (EMCV) that directs translation of HCV non-structural proteins (variously NS2 or NS3 to NS5B), and (4) the 3' NTR. Replicon-containing cells autonomously and persistently replicate HCV RNA that can be measured quantitatively by real-time qPCR. Therefore, the replicon system facilitates quantitative assessment of anti-viral activity by monitoring changes in HCV RNA replication in a cell-based assay.

HCV replicon-containing cells (Huh7/Clone A) were routinely maintained in Clone A growth medium (DMEM medium [Invitrogen], supplemented with 10% Fetal Bovine Serum, 1% Non Essential Amino Acids and 1 g/L G418). Test compounds were dissolved in dimethylsulfoxide (DMSO) to make 200× stock solutions for all doses prior to treatment.

For the HCV replicon assay, Huh7/Clone A cells were trypsinized from culture flasks, seeded in 1 ml of Clone A growth medium without G418 at $4\times10^4$ cells per well in 24-well plates and incubated at 37° C. in a humidified $CO_2$ (5%) incubator overnight. Following overnight incubation, compound solutions were added into wells in the same volume (5 µl of 200× compound stock per well) to give a final DMSO concentration of 0.5%. Three wells on each plate supplemented with 5 µl of DMSO served as untreated controls. For $IC_{50}$ determinations, compounds were tested at 7 serial dilutions in triplicates from the starting stock solutions. The plates were incubated at 37° C. for 48 hours. After incubation, cells were harvested, transferred to 96-well plates, and subjected to total RNA extraction using the RNA Isolation Kit (RNeasy 96, Qiagen) according to the protocol described by the manufacture's RNeasy 96 Handbook (Qiagen).

Total RNA eluted in 130 µl of RNase-free $dH_2O$ was quantitated by the RiboGreen Assay according to the supplier's protocol (Molecular Probe). Briefly, 5 µl of RNA samples were aliquoted in duplicate to a 96-well black microplate and a 96-well TaqMan Optical plate. RNA samples in the black microplate were mixed with 95 µl of diluted RiboGreen reagent (1:250 dilution in TE buffer) and sample fluorescence was measured using a fluorescence microplate reader at standard fluorescein wavelengths (excitation ~480 nm, emission ~520 nm). Ribosomal RNA (Molecular Probe) was used as standard.

TaqMan quantitative PCR (RT-qPCR) was used to quantitate the amount of HCV replicon RNA in each sample. The RT-qPCR reactions were performed in 25 µl on an ABI PRISM 7900 HT Sequence Detection System (Applied Biosystems). The reaction mixture contained 5 µl of total RNA (10-100 ng), 1× TaqMan Buffer A (Applied Biosystems), 5.5 mM $MgCl_2$, 1.2 mM dNTP mix, 0.625 U of AmpliTaq Gold (Applied Biosystems), 5 U of MMLV reverse transcriptase (Promega), 5 U of rRNasin (Promega), 300 nM each of the forward and reverse primers, and 100 nM TaqMan MGB probe. Primers and probe were designed to hybridize to a portion of the neomycin resistance gene (neo) in the replicon and the sequences are as follows: forward primer 5'-GGC-TACCTGCCCATTCGA-3'; reverse primer 5'-CCGGCTTC-CATCCGAGTAC-3'; MGB probe 5'-CCACCAAGC-GAAACA-3'. The RT step was performed at 48° C. for 30 min, followed by 10 min at 95° C. The thermal cycling program consisted of 40 cycles of 15 s at 95° C. and 1 min at 60° C. TaqMan raw data (Ct values) were analyzed using the Sequence Detection System (SDS) software, mathematically converted to HCV RNA genome amount and normalized to total RNA in each sample. The sample without compound treatment served as a control and the HCV replicon RNA level from untreated cells was defined as 100%. Compound inhibitory activity was determined as the ratio of the normalized HCV RNA amount in treated samples relative to the untreated control. Compound $IC_{50}$s were calculated using a standard 4 parameter curve fit model.

Results

The stereoisomer designated Formula I isomer A demonstrated 41% inhibition at 25 µM.

The stereoisomer designated Formula I isomer B demonstrated 33% inhibition at 25 µM.

The stereoisomer designated Formula I isomer C demonstrated 34% inhibition at 25 µM.

The stereoisomer designated Formula I isomer D demonstrated 29% inhibition at 25 µM.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound of Formula I:

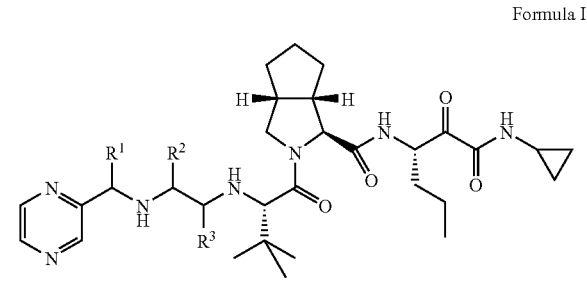

Formula I wherein:

$R^1$ is —$CF_2X$ having an absolute stereochemistry of R or S, in which X is hydrogen, fluoro or chloro, or X is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from the group consisting of fluoro and chloro; or $R^1$, and the carbon to which it is attached, form —C(=O);

$R^2$ is selected from the group consisting of alkyl of 1-6 carbon atoms and cycloalkyl of 3-8 carbon atoms, having an absolute stereochemistry of R or S, each of which is optionally substituted by 1, 2 or 3 groups selected from the group consisting of fluoro, chloro, and cycloalkyl of 3-6 carbon atoms, and $R^3$ is —$CF_2Y$ having an absolute stereochemistry of R or S, in which Y is selected from the group consisting of hydrogen, fluoro and chloro, or Y is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from the group consisting of fluoro and chloro; or R³, and the carbon to which it is attached, form —C(═O); with the proviso that R¹ and R³ are different;

or a pharmaceutically acceptable salt thereof.

2. The compound of claim 1, wherein R¹, and the carbon to which it is attached, form —C(═O) and R² is $C_{3-8}$cycloalkyl.

3. The compound of claim 2, wherein R³ is —CF₂Y, in which Y is hydrogen, fluorine, or chlorine.

4. The compound of claim 3, wherein R² is cyclohexyl in the (R) configuration and —CF₂Y is trifluoromethyl in the (S) configuration, structurally represented as:

IA

5. The compound of claim 3, wherein R² is cyclohexyl in the (R) configuration, and —CF₂Y is trifluoromethyl in the (R) configuration, which is structurally represented as:

IB

6. The compound of claim 3, wherein R² is cyclohexyl in the (S) configuration, and —CF₂Y is trifluoromethyl in the (S) configuration, which is structurally represented as:

IC

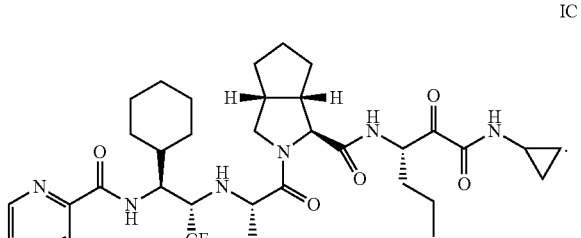

7. The compound of claim 3, wherein R² is cyclohexyl in the (R) configuration and —CF₂Y is trifluoromethyl in the (R) configuration, which is structurally represented as:

ID

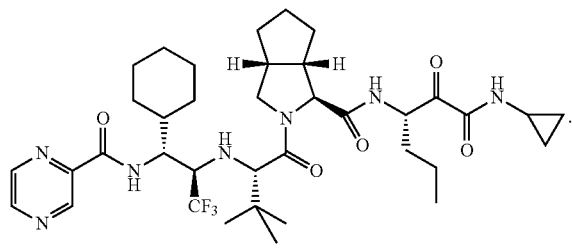

8. The compound of claim 1, wherein R² is $C_{3-8}$ cycloalkyl and R³, and the carbon to which it is attached, form —C(═O).

9. The compound of claim 8, wherein R¹ is —CF₂X, in which X is hydrogen, fluorine, or chlorine.

10. The compound of claim 9, wherein R¹ is trifluoromethyl in the (S) configuration and R² is cyclohexyl in the (S) configuration, which is structurally represented as:

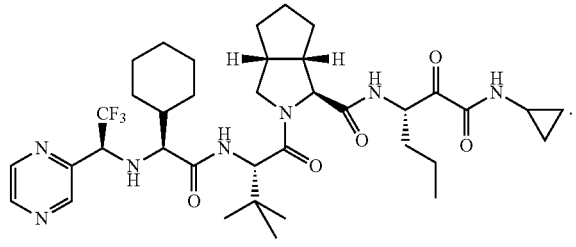

11. The compound of claim 9, wherein R¹ is trifluoromethyl in the (R) configuration and R² is cyclohexyl in the (S) configuration, which is structurally represented as:

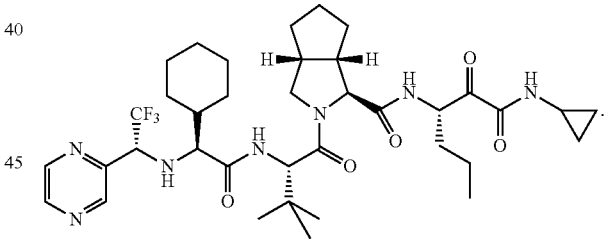

12. A pharmaceutical composition, comprising a therapeutically effective amount of a compound of claim 1 and at least one pharmaceutically acceptable excipient.

13. The pharmaceutical composition of claim 12, wherein the compound of claim 1 is selected from the group consisting of:

(1S,3aR,6aS)-2-((S)-2-((2S,3R)-3-cyclohexyl -1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((2R,3S)-3-cyclohexyl -1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((2S,3S)-3-cyclohexyl -1,1,1-trifluoro-3-(pyrazine-2-carboxamido)propan-2-ylamino)-

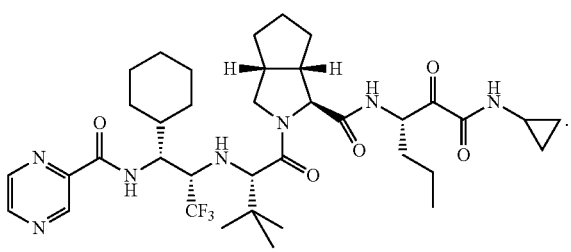

3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-(2R,3R)-(3-cyclohexyl-1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N—((S)-1-(cyclopropylamino)-1,2-dioxohexan-3-yl)octahydrocyclopenta[c]pyrrole-1-carboxamide; and (1S,3aR,6aS)-2-((S)-2-((S)-2-cyclohexyl-2-((R)-2,2,2-trifluoro-1-(pyrazin-2-yl)ethylamino)acetamido)-3,3-dimethylbutanoyl)-N—((S)-1-(cyclopropylamino)-1,2-dioxohexan-3-yl)octahydrocyclopenta[c]pyrrole-1-carboxamide.

14. A method of inhibiting protease cathepsin S in a mammal, comprising administering to a mammal in need thereof a therapeutically effective dose of a compound of Formula I:

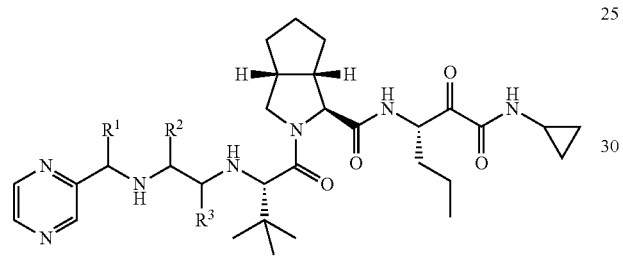

Formula I wherein:
R$^1$ is —CF$_2$X having an absolute stereochemistry of R or S, in which X is hydrogen, fluoro or chloro, or X is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from the group consisting of fluoro and chloro; or R$^1$ and the carbon to which it is attached, form —C(=O);

R$^2$ is selected from the group consisting of alkyl of 1-6 carbon atoms and cycloalkyl of 3-8 carbon atoms, having an absolute stereochemistry of R or S, each of which is optionally substituted by 1, 2 or 3 groups selected from the group consisting of fluoro, chloro, and cycloalkyl of 3-6 carbon atoms, and R$^3$ is —CF$_2$Y having an absolute stereochemistry of R or S, in which Y is selected from the group consisting of hydrogen, fluoro and chloro, or Y is alkyl of 1-4 carbon atoms optionally substituted by 1, 2, or 3 substituents selected from the group consisting of fluoro, chloro, and cycloalkyl of 3-8 carbon atoms, which is optionally substituted by 1, 2, or 3 substituents selected from the group consisting of fluoro and chloro; or R$^3$, and the carbon to which it is attached, form —C(=O); with the proviso that R$^1$ and R$^3$ are different; or a pharmaceutically acceptable salt thereof.

15. The method of claim 14, wherein the compound of Formula I is selected from the group consisting of:

(1S,3aR,6aS)-2-((S)-2-((2S,3S)-(3-cyclohexyl-1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((2R,3S)-(3-cyclohexyl-1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((2S,3S)-(3-cyclohexyl-1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((2R,3R)-(3-cyclohexyl-1,1,1-trifluoro-3-(pyrazine-2-carboxamido)propan-2-ylamino)-3,3-dimethylbutanoyl)-N—((S)-1-(cyclopropylamino)-1,2-dioxohexan-3-yl)octahydrocyclopenta[c]pyrrole-1-carboxamide;

(1S,3aR,6aS)-2-((S)-2-((S)-2-cyclohexyl-2-((S)-2,2,2-trifluoro-1-(pyrazin-2-yl)ethylamino)acetamido)-3,3-dimethylbutanoyl)-N—((S)-1-(cyclopropylamino)-1,2-dioxohexan-3-yl)octahydrocyclopenta[c]pyrrole-1-carboxamide; and (1S,3aR,6aS)-2-((S)-2-((S)-2-cyclohexyl-2-((R)-2,2,2-trifluoro-1-(pyrazin-2-yl)ethylamino)acetamide)-3,3-dimethylbutanoyl)-N—((S)-1-(cyclopropylamino)-1,2-dioxohexan-3-yl)octahydrocyclopenta[c]pyrrole-1-carboxamide.

* * * * *